US006899915B2

(12) United States Patent
Yelick et al.

(10) Patent No.: US 6,899,915 B2
(45) Date of Patent: May 31, 2005

(54) METHODS AND COMPOSITIONS FOR CULTURING A BIOLOGICAL TOOTH

(75) Inventors: Pamela C. Yelick, Concord, MA (US); John D. Bartlett, Acton, MA (US); Joseph P. Vacanti, Winchester, MA (US); Bjorn R. Olsen, Milton, MA (US); Phillip Stashenko, Medfield, MA (US)

(73) Assignees: President and Fellows of Harvard College, Cambridge, MA (US); General Hospital Corporation, Boston, MA (US); Forsyth Dental Infirmary for Children, Inc., Boston, MA (US)

( * ) Notice: Subject to any disclaimer, the term of this patent is extended or adjusted under 35 U.S.C. 154(b) by 0 days.

(21) Appl. No.: 09/997,734

(22) Filed: Nov. 29, 2001

(65) Prior Publication Data

US 2002/0119180 A1 Aug. 29, 2002

Related U.S. Application Data

(60) Provisional application No. 60/253,891, filed on Nov. 29, 2000.

(51) Int. Cl.[7] ................................................. A61C 13/08
(52) U.S. Cl. ................... 427/2.26; 433/202.1; 433/204; 264/19; 523/115
(58) Field of Search .............................. 427/2.26, 2.27; 433/202.1, 204, 215, 223; 264/19; 523/115; 521/50, 51, 55; 514/21; 424/435; 623/23.58, 23.72, 23.75

(56) References Cited

U.S. PATENT DOCUMENTS

| 5,098,891 A | * | 3/1992 | Hammarstrom et al. ...... 514/21 |
| 5,418,221 A | * | 5/1995 | Hammarstrom et al. ...... 514/21 |
| 5,863,297 A | * | 1/1999 | Walter et al. ............ 623/17.18 |
| 5,885,829 A | * | 3/1999 | Mooney et al. ............. 435/325 |
| 6,488,503 B1 | * | 12/2002 | Lichkus et al. ........... 433/202.1 |
| 2002/0022883 A1 | * | 2/2002 | Burg .............................. 623/8 |
| 2002/0192198 A1 | * | 12/2002 | Elia ......................... 424/93.21 |

OTHER PUBLICATIONS

"Annual Industry Report," *Implant Dentistry*, 9(3):192–194 (2000).
Baba et al., "Determination of enamel protein synthesized by recombined mouse molar tooth germs in organ culture," *Archives of Oral Biology* 41:215–219 (1996).
Backman et al., "Amelogenesis imperfecta: prevalence and incidence in a northern Swedish country," *Community Dent Oral Epidemiol*, 14(1):43–47 (1986).
Choi et al., "Studies of brush border enzymes, basement membrane components, and electrophysiology of tissue–engineered neointestine," *J. Pediatr. Surg.* 33:991–6; discussion 996–997 (1998).

(Continued)

Primary Examiner—James J. Seidleck
Assistant Examiner—Melanie Bissett
(74) Attorney, Agent, or Firm—Banner & Witcoff, Ltd.

(57) ABSTRACT

Tooth tissues include the pulp mesenchyme that forms the dentin and an epithelium that is responsible for enamel formation. Cells from these tissues were obtained from porcine third molars and were seeded onto a biodegradable scaffold composed of a polyglycolic acid—polylactic acid copolymer. Cell polymer constructs were then surgically implanted into the omentum of athymic nude rats so that the constructs would have a blood supply and these tissues were allowed to develop inside the rats. Infrequently, columnar epithelial cells were observed as a single layer on the outside of the dentin-like matrix similar to the actual arrangement of ameloblasts over dentin during early tooth development. Developing tooth tissues derived from such cell polymer constructs could eventually be surgically implanted into the gum of an edentulous recipient where the construct would receive a blood supply and develop to maturity, providing the recipient with a biological tooth replacement.

54 Claims, 20 Drawing Sheets

Tooth Scaffolds

PGA + PLLA

OTHER PUBLICATIONS

Choi and Vacanti, "Preliminary studies of tissue–engineered intestine using isolated epithelial organoid units on tubular synthetic biodegradable scaffolds," *Transplant Proc.* 29(1–2):848–851 (1997).

Chosack et al., "Amelogenesis imperfecta among Israeli Jews and the description of a new type of local hypoplastic autosomal recessive amelogenesis imperfecta," *Oral Surg Oral Med Oral Pathol,* 47:148–156 (1979).

DenBesten et al., "Development and characterization of an SV40 immortalized procine ameloblast–like cell line," *Eur. J. Oral Sci.* 107: 276–281 (1999).

Dummer et al., "Prevalence and distribution by tooth type and surface of developmental defects of dental enamel in a group of 15– to 16–year–old children in South Wales," *Community Dent Health,* 7(4):369–377 (1990).

Gronthos et al., "Postnatal human dental pulp stem cells (DPSCs) in vitro and in vivo," *Proc. Natl. Acad. Sci. USA* 97(25): 13625–13630 (2000).

Haffen et al., "Mesenchyme–dependent differentiation of epithelial progenitor cells in the gut," *J. Pediatr. Gastroenterol Nutr.* 6:14–23 (1987).

Isogai et al., "Formation of phalanges and small joints by tissue–engineering," *J. Bone Joint Surg. Am.* 81(3):306–316 (1999).

Kaihara et al., "Successful anastomosis between tissue–engineered intestine and native small bowel," *Transplantation* 67(2):241–245 (1999).

Kim and Vacanti, "The current status of tissue engineering as potential therapy," *Semin. Pediatr. Surg.* 8(3):119–123 (1999).

Stevens et al., *Theory and practice of histological techniques,* Stevens and Bancroft, Churchill Livingstone. New York, pp. 333–335, 1977 and 1982 Second Edition.

Thesleff et al., "Epithelial–mesenchymal interactions in tooth morphogenesis: the roles of extracellular matrix, growth factors, and cell surface receptors," *J. Craniofac. Genet. Dev. Biol.* 11:229–237 (1991).

Witkop, Jr. and Sauk, Jr., *Heritable defects of enamel, in Oral facial genetics,* R.E. Stewart and G.H. Prescott, Editors, C.V. Mosby Co., St. Louis, pp. 151–226 (1976).

Witkop, Jr. and Rao, "Inherited defects in tooth structures," *Birth Defects,* 7:153–184 (1971).

Xiao et al., "Dentinogenesis imperfecta 1 with or without progressive hearing loss is associated with distinct mutations in DSPP," *Nat. Genet.,* 27:201–204 (2001).

Zang et al., "DSPP mutation in dentiogenesis imperfecta Shields type II," *Nat. Genet.,* 27:151–152 (2001).

* cited by examiner

Tooth Scaffolds

PGA + PLLA

Removal of Porcine Third Molar

Removal of Porcine Third Molar

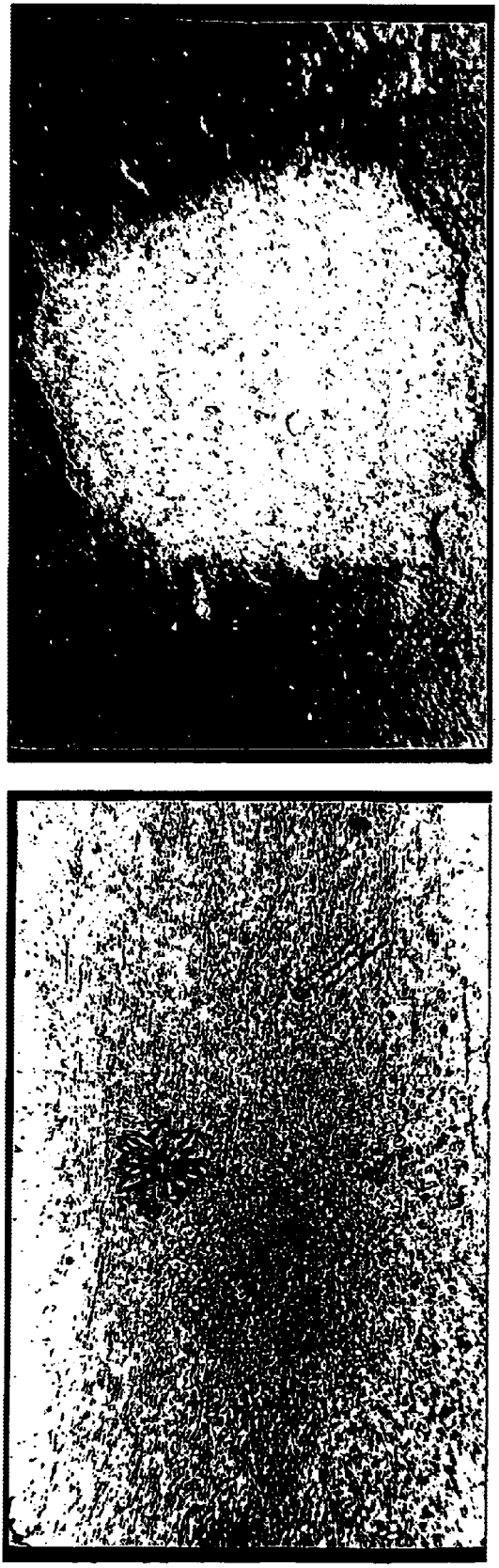
Fig. 7 Porcine Tooth Tissue Culture

Tissue Culture–Von Kossa Stain

Rat Radiographs - Implant, 7.5 weeks

Dissection of Tissue

Dissection of Tooth Tissue
7.5 weeks

Dissected Tooth Tissue - 7.5 Weeks

Goldner's Stain
Green = mineralized tissue

A

B

METHODS AND COMPOSITIONS FOR CULTURING A BIOLOGICAL TOOTH

RELATED APPLICATION

This application claims priority to U.S. Provisional Application Ser. No. 60/253,891, filed on Nov. 29, 2000.

STATEMENT OF GOVERNMENT INTEREST

This invention was funded by the Department of the Army, grant No. DAMD17-99-2-9001. The U.S. Government has certain rights to this invention.

BACKGROUND OF THE INVENTION

A developing molar tooth germ is encapsulated within the jaw from which it will eventually erupt. The tooth germ is first observed as a developing bud (bud stage), which fans out into a cap-like structure (cap stage), and finally develops into a bell-like form (bell stage). It is during the late bell stage that odontoblasts and ameloblasts differentiate and deposit the organic matrices of dentin and enamel. It has been well established that development of the tooth germ depends on reciprocal interactions between the epithelial and mesenchymal tissues (reviewed in: Thesleff et al., 1991).

Previously, Baba et al., (1996) have shown that molar tooth germs isolated from 16.5-day mouse embryos can be dissociated by enzymatic treatment. When the epithelial cells were separated from the mesenchymal cells, neither secreted enamel proteins nor cell proliferation were observed in either of the cultures. However, intriguingly, when the dissociated cells were cultured together, secretion of enamel proteins and cell proliferation were observed. Furthermore, the dissociated cells self-assembled back into a morphologically correct tooth germ that was successfully cultured for more than 20 days. The authors hypothesized that since the tooth germ lacked a blood supply, its development was prematurely terminated.

Tissue engineering is an interdisciplinary field that has evolved from the combined expertise of life sciences and engineering principles for the creation of biological substitutes that maintain, restore, or improve tissue function (Kim et al., 1999). Several tissues such as liver, intestine, bone, and cartilage have been successfully engineered (Kim et al., 1999). Dissociated cells from a tissue or organ have been used to seed biodegradable polymer scaffolds, which are implanted within a suitable host such that a sufficient blood supply would allow the cells to organize into higher ordered structures around the scaffold. The maintenance of cell structures, such as those present in organs, is not possible without a blood supply. Within a matter of weeks the scaffold dissolves and the dissociated cells will have organized into a tissue or organ that was pre-determined by the size and shape of the original scaffold. Tissue resembling small intestine, consisting of a neomucosa lined with smooth muscle, columnar epithelium, and goblet cells having villus-like structures, have been generated using the above approach (Choi and Vacanti, 1997). Epithelial-mesenchymal cell interactions are as essential for developing teeth as they are for the proper development of intestinal tissues. In the tooth, mesenchymal cells form the dentin while cells of epithelial origin form the enamel. Although each mineralized tissue is formed from its respective cells of origin, epithelial-mesenchymal interactions are required to initiate the mineralization process.

The demonstrated establishment of bioengineered epithelial-mesenchymal cell-cell communications (intestine) and the synthesis of mineralized tissues (bone and cartilage) necessary for growing teeth have already been accomplished. A significant need exists for replacement teeth as observed from the common use of dental implants (year 2000 projected number of dental implant procedures was 910,000 with a compound annual growth rate of 18.6% from 1998 to 2005, (Annual Industry Report, 2000). A biological tooth substitute that is properly formed and integrated into the jaw of a human patient would outlast synthetic dental implants since a living tooth responds to its environment by migrating to maintain a proper bite, and has some regenerative properties in response to injury. Implants do not have these capabilities. In addition, people who have genetically inherited enamel (amelogenesis imperfecta) or dentin (dentinogenesis imperfecta) defects could be greatly helped by the availability of functional tooth replacements.

Amelogenesis imperfecta (AI) is a collection of genetic defects manifested by the malformation of dental enamel. One out of every 7,000 to 14,000 children are affected (Backman and Holm, 1986; Chosack et al., 1979; Dummer et al., 1990; and Witkop Jr. and Sauk Jr., 1976). By definition, the disorder must be limited to the dental apparatus and cannot be associated with more generalized defects (Witkop Jr. and Rao, 1971).

Dentinogenesis imperfecta 1 (DGI1) is an autosomal dominant dental disease characterized by abnormal dentin production and mineralization (Xiao et al., 2001). Dentinogenesis imperfecta Sheilds type II (DGI-II) is also an autosomal dominant disorder in which both the primary and permanent teeth are affected. It occurs with an incidence of 1:8,000 live births (Zang et al., 2001).

Recent advances in tissue engineering have demonstrated that organs derived from both epithelial and mesenchymal cells can be fashioned into a pre-determined shape and size and can be provided with a blood supply (Choi et al., 1998; Choi and Vacanti, 1997). Specifically, small pieces (organoid units) of enzymatically digested 6-day-old rat intestine were seeded onto sheets of non-woven polyglycolic acid (PGA) scaffolds and were incubated in culture for various times. Next, they were implanted into the omentum of syngeneic rats. The PGA provided the biodegradable three-dimensional scaffold and implantation into the omentum provided the blood source. The organoid units proliferated and generated larger complex cystic structures that possessed much of the morphology of the mature intestine. A key to the success of the implants was not to delay the in vitro culture time more than is necessary for the organoids to become firmly attached to the scaffold (Choi and Vacanti, 1997). Later, the engineered intestines were further characterized to show that they became phenotypically mature (Choi et al., 1998) and that successful anastomosis occurred between the tissue-engineered intestine and the native small bowel (Kaihara et al., 1999). Since as for the tooth, the intestine is also derived from the interactions of both epithelial and mesenchymal tissues (Haffen et al., 1987), these data provide strong evidence that the dissociated tooth germ may also become fully mature through the techniques of tissue engineering.

A major difference between the tooth and the intestine is that the tooth becomes a mineralized tissue whereas the intestine does not. However, this is not a major technological difficulty since virtually the same tissue-engineering technique used to generated the intestine was also used to engineer mineralized phalanges with joints (Isogai et al., 1999). The phalanges were specifically designed to have a human shape and were shown to possess mature articular cartilage and subchondral bone. Thus, we are generating a tissue-engineered tooth by using techniques similar to those that were used successfully to generate an intestine and phalanges with joints.

The practice of dentistry would be revolutionized, by providing the patient and oral surgeon a means to replace a defective or diseased dentition with a healthy and permanent biological dentition. These studies could yield new insight into the regulation of enamel formation and may provide a means of generating tissue engineered dentin or enamel materials that could be used to repair unhealthy teeth.

DESCRIPTION OF THE INVENTION

Figure 1:
FIG. 1 shows tooth scaffolds.
Figure 1:
Figure 2:
FIG. 2 shows tooth scaffolds-PGLA.
Figure 3:
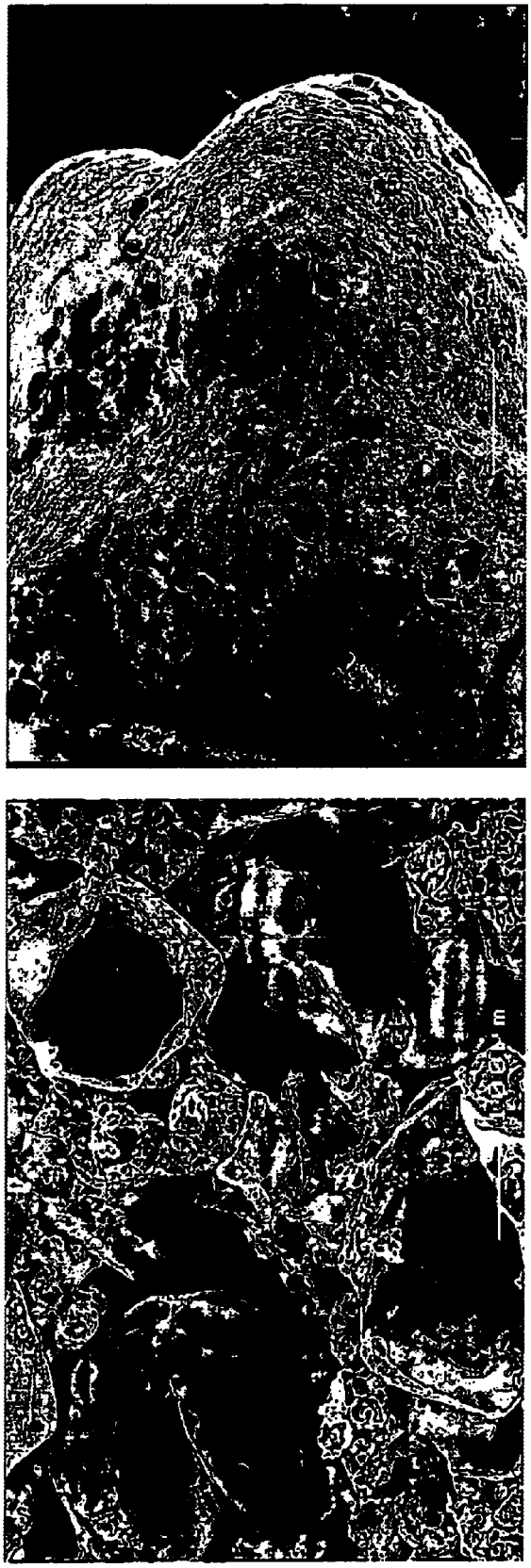
FIG. 3 shows scanning electron micrographs of a PLGA scaffold plus salt.
Figure 4:
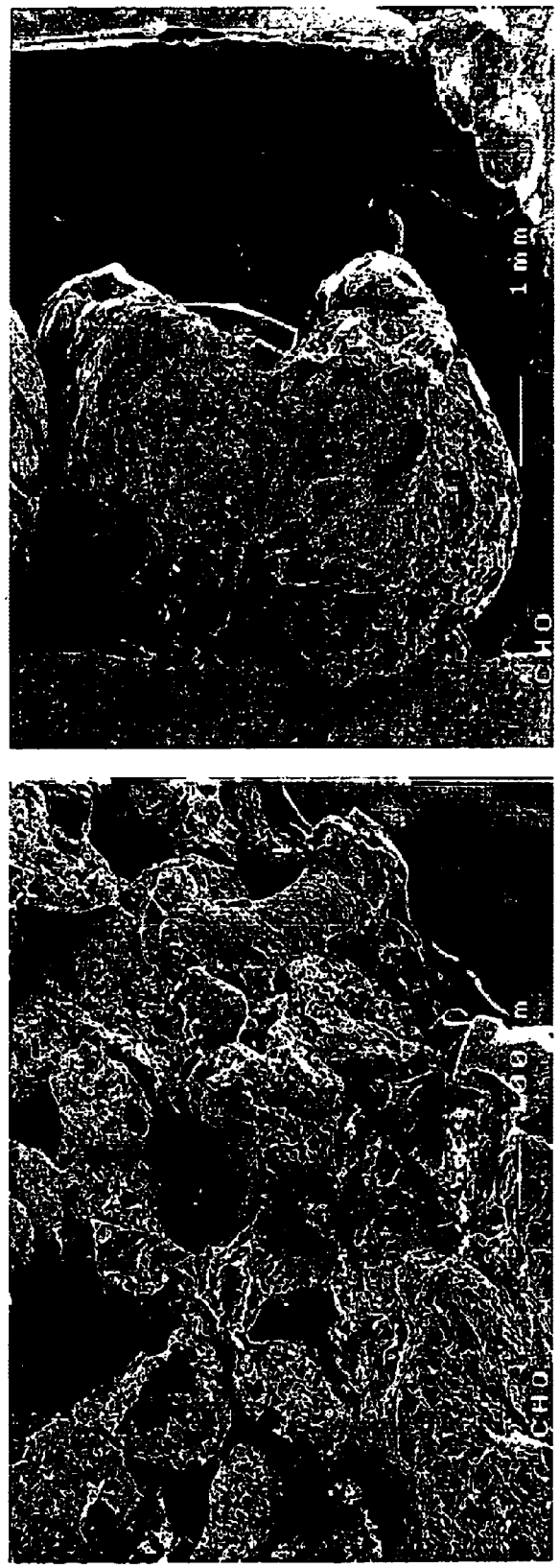
FIG. 4 shows scanning electron micrographs of a PLGA scaffold plus sugar.

Our goal is to produce a biological tooth replacement using tissue-engineering methodology based on seeding dissociated tissues onto biodegradable polymer scaffolds, and allowing the cell/polymer constructs to develop into tooth tissues inside of a suitable host. Polymer scaffolds are molded in the shape of human teeth using polyvinylsiloxane molds and seeded with dissociated tissues from unerupted porcine third molars. Cell/polymer constructs are implanted into the omentum of athymic rats so that the developing tooth tissues receive an adequate blood supply. Cells dissociated from the enamel organ and pulp organ and cells from tissue cultures derived from tooth tissues, are seeded onto molded tooth-shaped polymers, and implanted for development in rat hosts. Analysis of the resulting tooth tissues is performed using histological staining methods such as Von Kossa (calcification), Goldner's (ossification), and Van Gieson's (collagen). Immunohistochemical staining is also performed using antibodies specific for tooth epithelial markers (keratin, amelogenin) and mesenchymal markers (osteocalcin, bone sialoprotein and dentin sialophosphoprotein). The results of these experiments establish the identity of ameloblasts that are responsible for enamel formation, and odontoblasts that are responsible for dentin formation, within the engineered tooth tissues. Immunofluorescence using the above markers is applied to cells in culture to characterize them prior to seeding on polymer scaffolds. In situ hybridization is used to detect the presence of DSPP mRNA, a marker for odontoblast cells, and to help distinguish between tissues of the rat host and developing porcine tooth tissues.

Table 1 provides an overview of the invention. Table 2 provides an overview of the polymer scaffold preparation.

TABLE 1

Experimental Approach

| | |
|---|---|
| Remove porcine third molar | Surgical implantation of seeded polymers |
| Mince tissue and treat enzymatically | Incubation in rat omentum |
| Mild mechanical dissociation | X-ray rats |
| Count cells | Dissect tooth tissue |
| Polymer seeded with cells and "organoids" | Histology |

TABLE 2

Polymer Scaffold Preparation

Polyglycolic acid (PGA), poly-L-lactic acid (PLLA), polylactic-co-glycolic acid (PLGA)
Dissolve polymer in chloroform or dioxane
NaCl or glucose crystals added to increase porosity (PLGA scaffolds only)
Combine polymer solution and crystals in tooth mold
Freeze-dry to evaporate solvent
Place scaffold in water to dissolve salt/sugar

EXAMPLE

A. Materials and Methods

Chemicals. polyglycolic acid (PGA), poly-L-lactic acid (PLLA), poly-L-lactide-co-glycolide (PLGA), chloroform, dichloromethane, polyvinylsiloxane dental impression material (Reprosil), sodium chloride, Hank's Balanced Salt Solution (HBSS), phosphate-buffered saline solution (PBS), Dulbecco's Modified Eagle Medium (DMEM), fetal bovine serum, Glutamax, penicillin, streptomycin, sorbitol, 0.9% saline solution, iodine solution (Povidine), 70% ethanol, collagen (type I), 0.01 M hydrochloric acid, collagenase, dispase, ketamine, xylazine (Rompun).

Tissues. Human incisors and molars, six-month-old porcine third molar tooth tissue.

Preparation of tooth molds. Extracted human incisors and molars were used to cast negative impression tooth molds in polyvinylsiloxane dental impression material (Reprosil). Once the impression material hardened, the teeth were removed by cutting an opening in one side of the mold with a razor blade. This method leaves a tooth-shaped cavity inside the impression material which can be filled with polymer solution for the preparation of biodegradable tooth scaffolds.

Preparation of polymer tooth scaffolds. PGA mesh material was broken up into 1–2 mm flakes and packed into the cavity of a tooth mold to fill it completely. The remainder of the cavity volume was filled with a 3% w/w PLLA solution in chloroform. The PGA/PLLA mixture was heated to approximately 400° F. for 5 minutes to bond the two polymers and then lyophilized for 48 h. For PLGA tooth scaffolds, PLGA crystals were first dissolved in chloroform to 5% w/w. Negative tooth molds were packed to half-capacity with sodium chloride crystals (75–150 µm) and the remainder of the mold volume was filled with 5% PLGA solution. Sodium chloride crystals were added to create a thick slush in the PLGA solution and the mixture was lyophilized for 48 h. Scaffolds were removed from the molds and placed in distilled water for 24 h to leach out the salt crystals leaving behind a porous PLGA sponge material in the shape of a tooth.

Tissue dissociation. Fresh pig jaw dissected from a freshly slaughtered six-month-old pig was placed on ice for transport. The jaw was split in two and muscle and connective tissue were removed from the bone using a razor blade. A dental drill fitted with a spherical bit was used to drill holes along the lingual side of the bone surface along lines adjacent to the regions harboring the $3^{rd}$ and $2^{nd}$ unerupted molars. Bone chisels were used to break the bone in between the drilled holes and then the resulting bone flap was pried and lifted away to expose the unerupted molars. A dental probe was used to carefully lift out the $3^{rd}$ molar and connective tissue was cut with surgical scissors. The molars were placed in ~50 ml of Hank's balanced salt solution (HBSS) and kept at 4° C. in 50 ml sterile conical tubes.

Prior to mincing the tissues, the immature tooth cusps were removed and discarded. The remaining enamel and pulp organ tissues were minced into 2–3 mm$^3$ pieces in a sterile Petri plate in HBSS. Tissues were washed 5 times in HBSS, minced into <1 mm$^3$ pieces and then treated with 1.5 units of Vibrio alginolyticus collagenase and 12 units of *Bacillus polymyxa* dispase for 25 minutes at room temperature. Gentle mechanical dissociation of tissues was achieved by pipetting the suspension up and down in a 25 ml pipette for 10 min followed by 15 min with a 10 ml pipette. Tissues were washed five times in DMEM (containing 2.5% FBS, 2% sorbitol, Glutamax, 50 units/ml penicillin, 50 □g/ml streptomycin) and then cells were counted using a hemacytometer. Typical cell yields were 2.0×10$^6$ cells/ml.

Seeding of biodegradable polymer scaffolds. PGA/PLLA and PLGA tooth scaffolds were coated with collagen overnight at 4° C. in a 1 mg/ml type I collagen solution in 0.01 M HCl. Scaffolds were washed three times in PBS then three times in DMEM+supplements (see above). ~2.0×10$^6$ cells were seeded onto each tooth scaffold and cells were given at least 1 hour to attach. Laparotomies were performed on athymic nude rats and seeded scaffolds were implanted into the omentum to provide a blood source for the developing tooth tissues. Tissues were allowed to develop inside the host animals for 7–20 weeks before they were sacrificed and the engineered tissues harvested.

B. Results

The results of these experiments are generally summarized in Table 4.

TABLE 4

Tooth Tissue Engineering Schedule

| Date | Material | Shape | Time (weeks) | Status |
|---|---|---|---|---|
| Aug. 10, 2000 | Poly-glycolide (PGA) | Short tube<br>Long tube<br>Human incisor | 8.5 | Sacrificed<br>Sacrificed<br>Alive |
| Aug. 23, 2000 | PGA + poly-L-lactide (PLLA) | Incisor<br>Incisor<br>Molar | 6.5 | Deceased<br>Alive<br>Alive |

TABLE 4-continued

Tooth Tissue Engineering Schedule

| Date | Material | Shape | Time (weeks) | Status |
|---|---|---|---|---|
| Sep. 7, 2000 | Poly-L-lactide-co-glycolide (PLGA) + salt crystals | Molar<br>Incisor | 4.5 | Alive<br>Alive |
| Sep. 27, 2000 | PLGA + salt or sugar crystals | Molar<br>Molar<br>Incisor<br>Incisor | — | Deceased<br>Deceased<br>Deceased<br>Deceased |

Polymer Tooth Scaffolds. Human incisors and molars were used to make negative impressions in Reprosil dental impression material. PGA mesh material was then broken into flakes and these flakes were used to completely fill the tooth mold. The remainder of the mold cavity volume was filled with a 3% PLLA solution in chloroform. The PGA/PLLA mixture was heated to approximately 400° F. for 5 minutes to bond the two polymers and then lyophilized for 48 hours. The PLGA tooth scaffolds were made as described in the Materials and Methods section.

Tooth Tissues. Immediately after slaughter, mandibles from six-month old pigs were collected at the slaughterhouse and transported on ice to the laboratory. The second and third unerupted molars from each hemimandible were dissected from the jawbone and were immersed in separate vials containing Hanks balanced salt solution. All teeth were kept at 4° C. prior to dissociation of the tissues. The enamel and pulp organ tissues were minced, washed, minced again, and treated with collagenase/dispace in order to obtain the greatest amount of single cells in suspension. The cells were then washed several more times and were resuspended in DMEM containing 2.5% FBS and 2% sorbitol.

Seeding of Biodegradable Polymer Scaffolds. PGA/PLLA and PLGA tooth scaffolds were coated with collagen overnight at 4° C. in a type I collagen solution in 0.01 M HCl. Scaffolds were washed three times in PBS then three times in DMEM plus FBS and sorbitol. Cells were seeded onto each tooth scaffold and were given at least 1 h to attach. Laparotomies were performed on athymic nude rats and seeded scaffolds were implanted into the omentum to provide a blood source for the developing tooth tissues. The tissues were allowed to develop inside the host animals for 7–20 weeks before they were sacrificed and the engineered tissues harvested.

Characterization of Bioengineered Tooth Tissues. Host animals were sacrificed after 7.5 weeks of development and the tooth tissues were dissected, preserved and fixed in formalin, and embedded in paraffin for histological sectioning. Tissue sections were stained with hematoxylin and eosin and counterstained by the Von Kossa method to identify mineralized tissues. Tissues were also stained by the method of van Gieson to identify areas of ossification and were stained by the method of Goldner to detect the presence of collagen.

Histological sections of engineered tooth tissues revealed an organization analogous to the early tooth bud. Present was a layer of collagenous matrix that appeared similar to that observed in dentin or bone. The surrounding region of mesenchyme looked like what is observed in pulp tissue. Infrequently, a single layer of columnar epithelium was observed on the outer face of the collagenous matrix, resembling epithelial ameloblast cells, which form dental enamel. Some regions of the collagenous matrix stained positively for the presence of calcified mineral deposits suggesting that biomineralization had occurred.

C. Discussion

Preliminary results demonstrate successful use of porcine odontogenic cells to generate replacement molar and incisor teeth. Mineralization was observed in a four week-old tissue culture of the dissociated porcine third molar tissues, suggesting that a mixture of dissociated tooth tissue cells can spatially reorganize themselves in vitro, and generate calcified deposits. Dissociated porcine tooth tissue cells were seeded onto collagen-coated PGA scaffolds and implanted into the omenta of rat hosts. Histological analysis of 7.5-week-old implanted PGA scaffolds revealed an organization similar to that of the early tooth bud. A layer of collagenous matrix similar to dentin or bone surrounded the mesenchyme tissue. This resembles what naturally occurs in pulp tissue. Rarely, a single layer of columnar epithelium was observed on the outer face of the collagenous matrix. This is similar to the organization of enamel-forming epithelium just prior to the formation of dental enamel. The presence of calcified mineral deposits suggests that biomineralization had occurred. These results demonstrate that it is possible to grow mineralized tooth tissues using biodegradable polymer tooth scaffolds seeded with tooth bud cells. Thus, we have demonstrated that by use of the tissue engineering techniques described here, it is possible to grow mineralizing tissues that resemble those of the developing tooth.

Preparation of Tooth Molds

Rationale. Tooth molds are used to prepare scaffolds in the shapes of individual human teeth so that the seeded tooth cells will form a tooth of a predetermined shape and size.

Experimental approach. Extracted human incisors and molars are used to create tooth molds in polyvinylsiloxane dental impression material (Reprosil). Once the impression material has hardened, the teeth are removed by cutting an opening in one side of the mold with a razor blade. This method leaves a tooth-shaped cavity inside the impression material, which can be filled with polymer solution for the preparation of biodegradable tooth scaffolds.

Preparation of Polymer Tooth Scaffolds

Rationale. Polymer scaffolds of optimal porosity are necessary so that the seeded cells can migrate through the scaffold to their appropriate positions to begin forming the tissue-engineered tooth.

Experimental approach. PGA mesh material is broken into 1 $mm^2$ flakes and packed into the cavity of a tooth mold to fill it completely. The remainder of the cavity volume is filled with a 3% w/w PLLA solution in chloroform. The PGA/PLLA mixture is heated to approximately 400° F. for 5 min to bond the two polymers and then is lyophilized for 48 h. For PLGA tooth scaffolds, PLGA crystals will first be dissolved in chloroform to 5% w/w concentration. Tooth molds are packed to half-capacity with sodium chloride crystals (75–150 $\mu$m) and the remainder of the mold volume is filled with 5% PLGA solution. Sodium chloride crystals are added to create a thick PLGA slush, and the mixture is lyophilized for 48 h. Scaffolds are removed from the molds and placed in distilled water for 24 h to dissolve salt crystals, leaving behind a porous PLGA sponge material in the shape of a tooth.

Isolation and Preparation of Porcine Tooth Tissues for Seeding onto Biodegradable Polymer Scaffolds Rationale. Optimized procedures for dissociating tooth tissues for seeding onto the polymer scaffold are necessary so that both the epithelial and mesenchymal cells will attach, migrate to their appropriate positions, and form their respective mineralized tissues (enamel and dentin).

Experimental approach. A jaw dissected from a freshly slaughtered six-month old pig is placed on ice for transport from the farm (Athol, Mass.) to The Forsyth Institute. The jaw is split at the midline. Muscle and connective tissue are removed from the bone using a razor blade. A dental drill fitted with a spherical burr is used to drill holes along the jaw (lingual side) surrounding the region of the M2 and M3 unerupted molars. Bone chisels are then used to break the bone in between the drilled holes, and the resulting bone flap is removed to expose the unerupted molars. A dental probe is used to carefully lift out M2 and M3 tooth sacs, and the connective tissue is removed with surgical scissors. The molars are placed in ~50 ml of Hank's balanced salt solution (HBSS) and kept at 4° C. in 50 ml sterile conical tubes. When present, immature tooth cusps are removed and discarded, and the remaining enamel and pulp organ tissues are minced into 2–3 $mm^3$ pieces in a sterile Petri dish in HBSS. Tissues are washed 5 times in HBSS, minced into <1 $mm^3$ pieces and treated with 1.5 units of *Vibrio alginolyticus* collagenase and 12 units of *Bacillus polymyxa* dispase for 25 min at room temperature. Gentle mechanical dissociation of tissues is achieved by gentle pipetting with a 25 ml pipette for 10 min followed by 15 min with a 10 ml pipette. The dispersed cells are washed five times in DMEM (containing 2.5% FBS, 2% sorbitol, Glutamax, 50 units/ml penicillin, 50 $\mu$g/ml streptomycin) and pelleted by gentle centrifugation at approximately 400×g and counted using a hemacytometer. Typical cell yields are approximately $5.0 \times 10^6$ cells/ml.

Molded PGA/PLLA and PLGA tooth scaffolds are coated with collagen overnight at 4° C. in a 1 mg/ml type I collagen solution in 0.01 M HCl. Scaffolds are washed three times in PBS then three times in DMEM+supplements (see above). Approximately $2.0 \times 10^6$ cells are seeded onto each tooth scaffold and allowed to attach for at least 1 hour. Laparotomies are performed on athymic nude rats and the seeded scaffolds are implanted into the omentum, providing a blood source for developing tooth tissues. The implants are allowed to develop inside the host animals for 7–35 weeks before the engineered tissues are harvested.

To our knowledge, no study has ever examined the feasibility of growing biological teeth using dissociated tooth tissues seeded on biodegradable polymer scaffolds. One group has used hydroxyapatite/tricalcium phosphate powder mixed with cultured dental pulp cells to generate a small amount dentin matrix secreted by odontoblast-like cells six weeks after subcutaneous implantation in nude mice (Gronthos et al., 2000). However, using our approach we have obtained structures resembling developing and mature teeth with dentin secreted by odontoblasts, enamel secreted by ameloblasts, a well-defined pulp chamber and putative cementoblasts embedded in a cementum matrix (see Preliminary Data). Thus, our approach has demonstrated that it is possible to engineer developmentally advanced tooth tissues.

Preliminary Data

In vitro analysis of dissociated tooth tissues. Six-month old porcine third molars (M3) were dissociated into cell suspensions and grown in culture for a period of four weeks. The cell cultures exhibited extensive mineralization, as measured by Von Kossa staining (data not shown), suggesting that the dissociated tooth tissues could spatially reorganize themselves in vitro to form calcified deposits.

Figure 17:
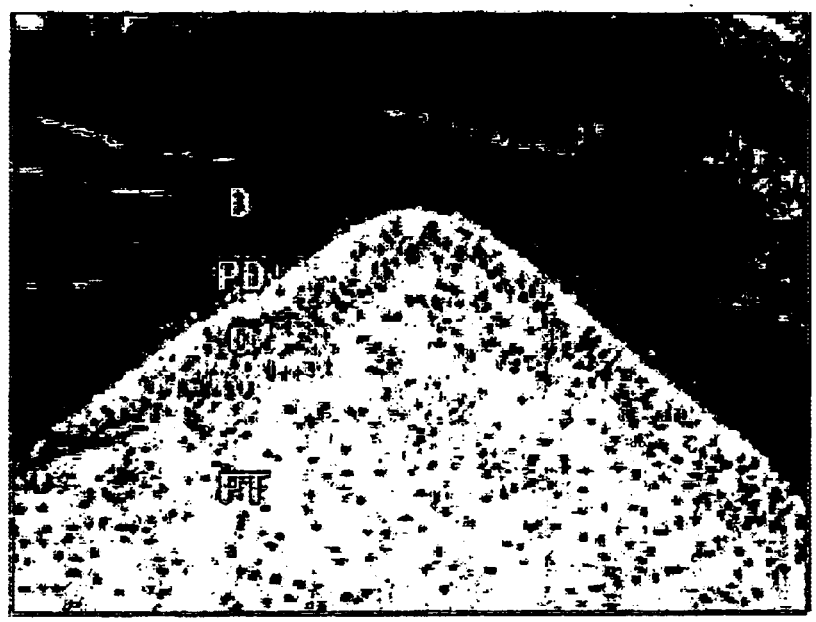
FIG. 17 shows a cell seeded incisor scaffold 20 weeks post-implantation.

Analysis of Seeded and Implanted Biodegradable Scaffolds Twenty week implant. Dissociated enamel and pulp cells obtained from a 6 month-old pig third molar were seeded onto a PGA scaffold molded in the shape of a human incisor of approximately 1 cm by 0.5 cm in size. The cell/polymer construct was implanted into the omentum of a nude rat host and allowed to develop for 20 weeks. At this time, histological analysis revealed small tooth-shaped tissues within the implant, which were similar in appearance to that of a very small cusp tip (FIG. 17). We observed mineralized dentin-like tissue (D) and beneath the dentin, was a pre-dentin-like layer (PD) that appeared to be secreted by odontoblast-like cells (O). Vascularized mesenchyme resembling that of pulp tissue (PT) filled the remainder of the pulp cavity (FIG. 17).

Figure 18:
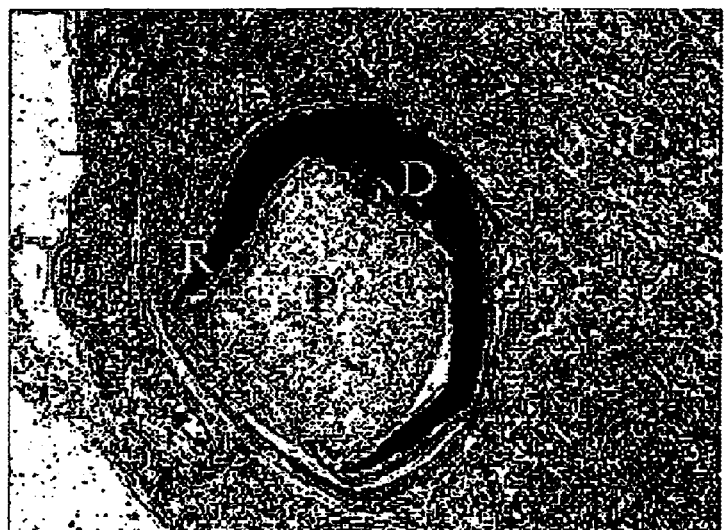
FIG. 18A shows a histological section of a 20-week tooth bud stained with hematoxylin and eosin and then counterstained by the method of Von Kossa.
FIG. 18B shows the root tip of the bud of FIG. 18A, showing columnar odontoblasts and Hertwig's root sheath.
Figure 18:
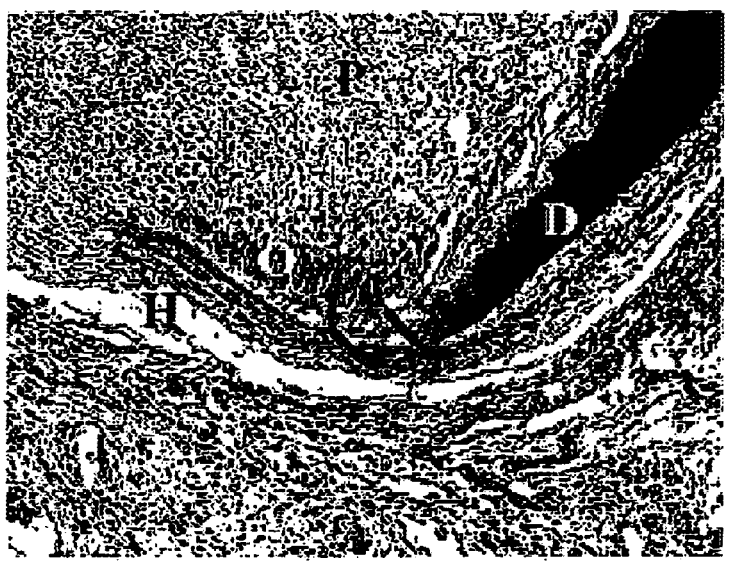

The cellular organization of another 20 week implant clearly resembles that of an early bell stage tooth bud (FIGS. 18A–B). The tooth tissue was ~2 mm in diameter and exhibited distinct coronal and apical organization, with recognizable cusps and root tips. Putative odontoblasts (O) lined the inner surface of an apparently collagenous dentin matrix (D) (FIGS. 18 A–B) and putative Hertwig's root sheath epithelia (H) was also present adjacent to the developing root tips (FIG. 18B).

In summary, the 20-week tooth tissues contained putative pre-dentin and mineralized dentin components, and vascularized mesenchymal cells resembling pulp tissue populated the pulp chamber. In this twenty-week implant no ameloblast-like epithelial cells were observed on the outer face of the putative dentin tissue.

Figure 19:
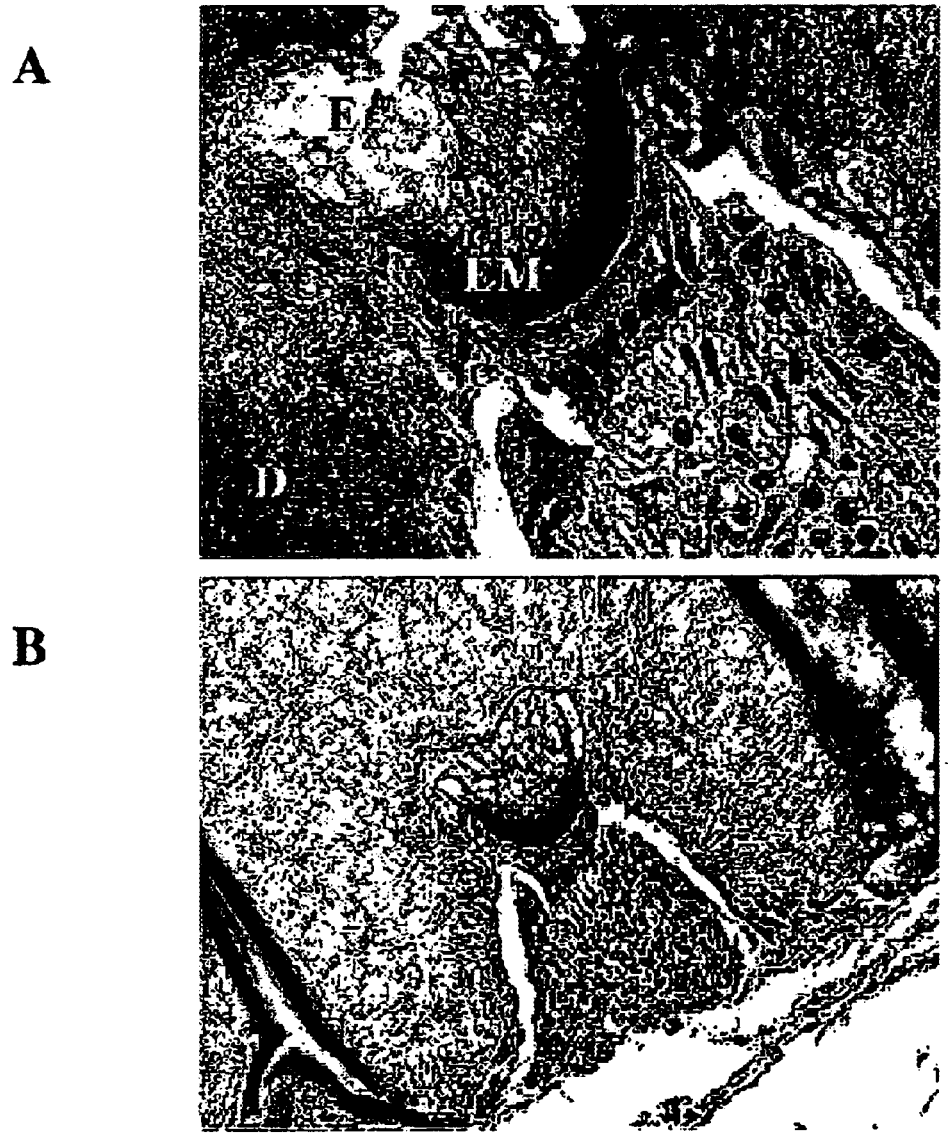
FIG. 19A shows an engineered tooth with dentin, enamel, and ameloblasts stained with hematoxylin and eosin.
FIG. 19B shows an engineered tooth with dentin, enamel, and ameloblasts stained by Goldner's method.

Twenty-five week implant. A tooth tissue implant consisting of a PGA polymer scaffold molded in the shape of a human incisor seeded with ~2.0×10$^6$ porcine tooth tissue cells was dissected from a nude rat at 25 weeks post implantation. The tissue was fixed in neutral formalin, embedded in paraffin, sectioned and then stained with hematoxylin and eosin (FIG. 19A). A tooth bud with a diameter of 2 mm was discovered within the excised tissue. The interior core of the tooth bud consisted of pulp-like mesenchymal cells lined with columnar odontoblasts which were adjacent to a dentin-like layer, as has been observed in previous 20-week tooth buds (see FIGS. 17 and 18A–B). In some locations a different mineralizing layer (E, EM) was observed (FIG. 19A) which closely resembled decalcified porcine enamel. A darkly stained region was found directly adjacent to numerous columnar cells possessing polarized nuclei which closely resembled ameloblasts (A). This densely stained region was thought to be enamel matrix since the staining was significantly reduced in the deeper layers just as it is for naturally forming enamel. The same tissue was stained by the method of Goldner (FIG. 19B) which stains osseous tissues blue-green while the mature dental enamel stains a bright red color (Dr. Ziedonis Skobe, personal communication) Thus, after 25 weeks of implant development, we have obtained engineered tissues that are composed of the two major mineralizing structures of the tooth: the dentin and enamel.

Figure 20:
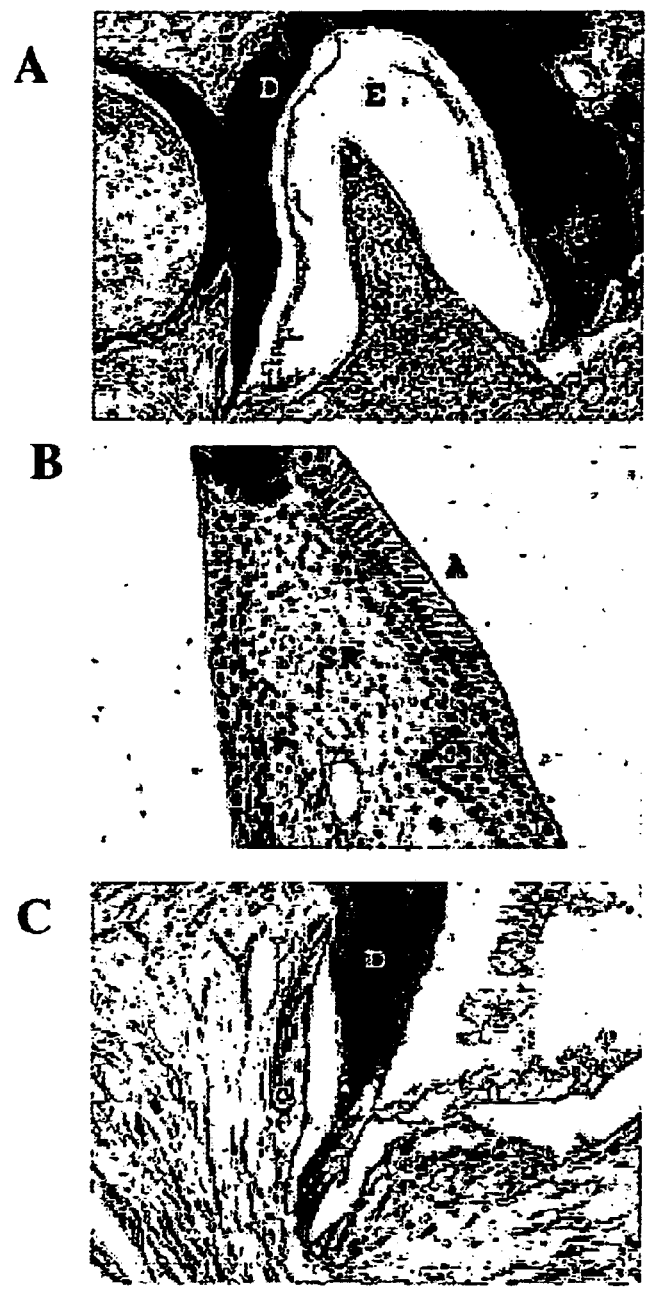
FIG. 20A shows a histological section of a 30-week implant stained with hematoxylin and eosin, having demineralized enamel interior to the dentin.
FIG. 20B shows an ameloblast cell layer adjacent to enamel space of the implant of FIG. 20A.
FIG. 20C shows the cementum of the implant of FIG. 20A with embedded nuclei of putative cementoblasts.
Figure 1:
Figure 1:
Figure 2:
Figure 3:
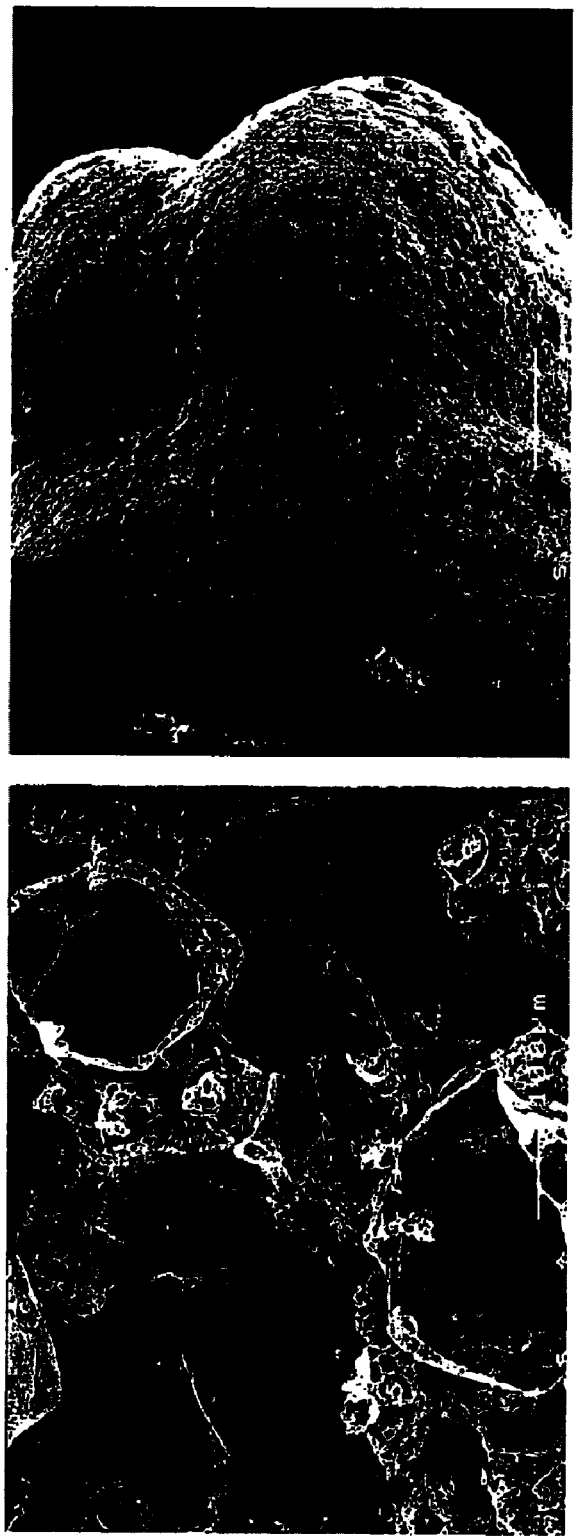
Figure 4:
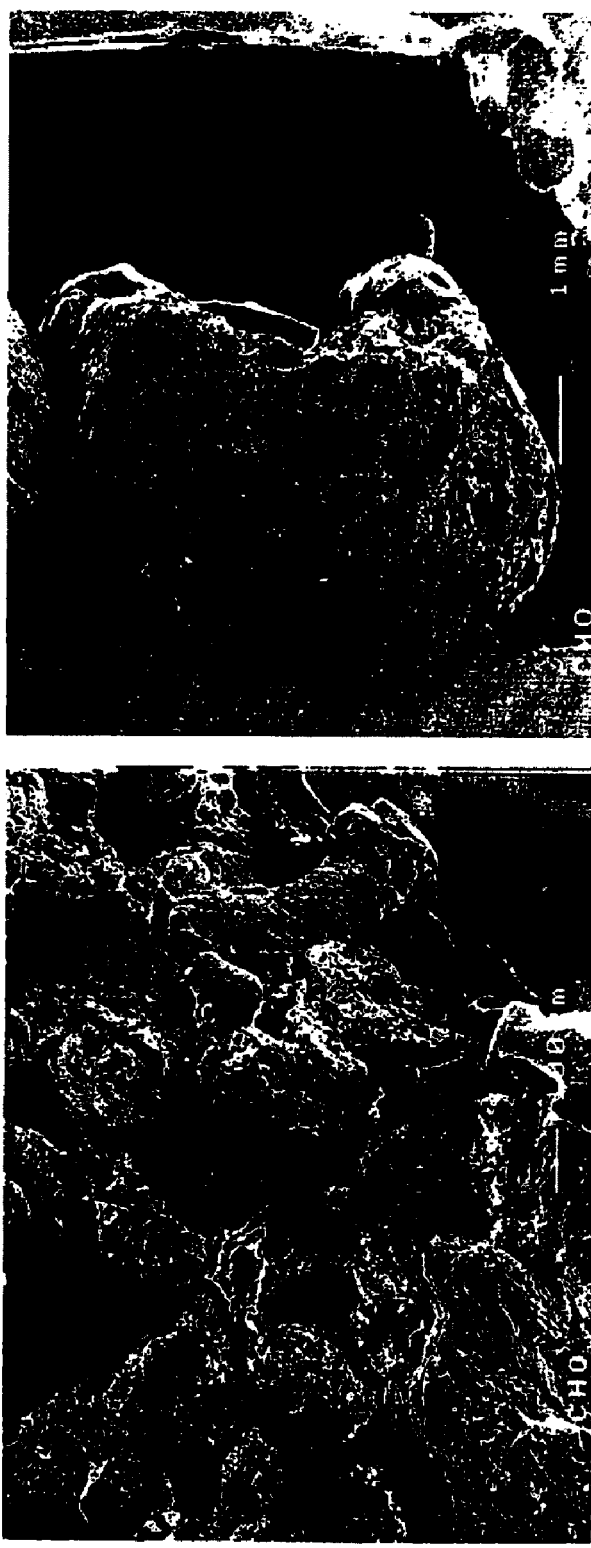
Figure 5:
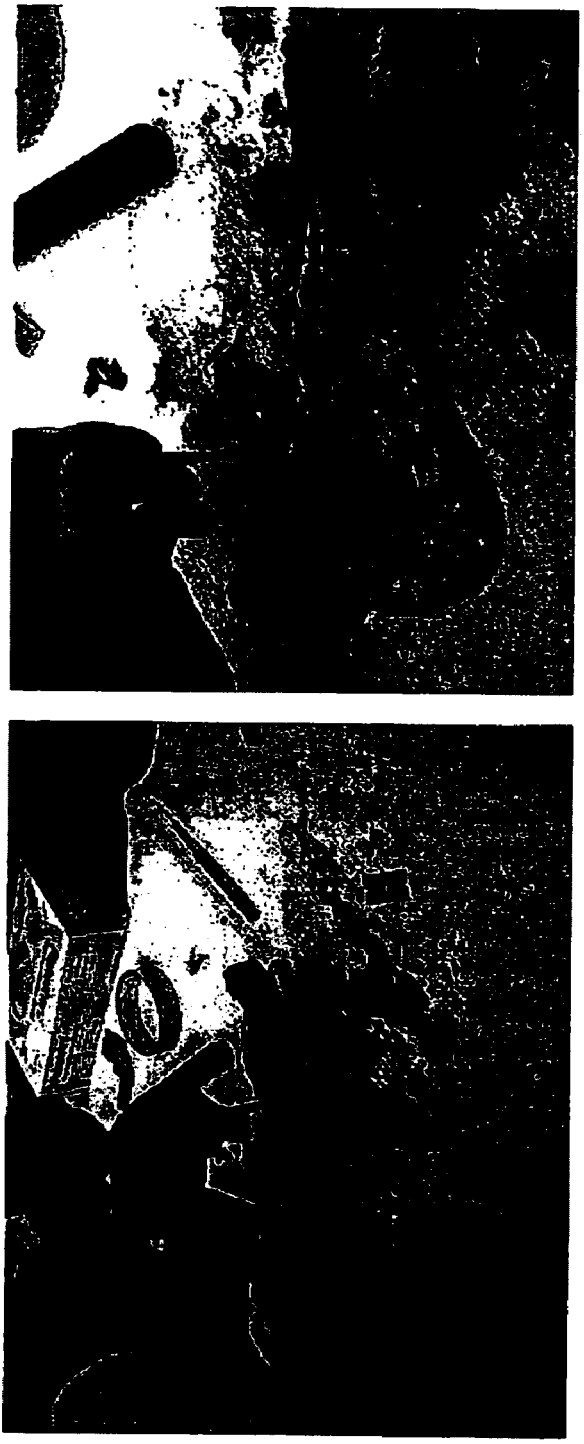
Figure 6:
Figure 7:
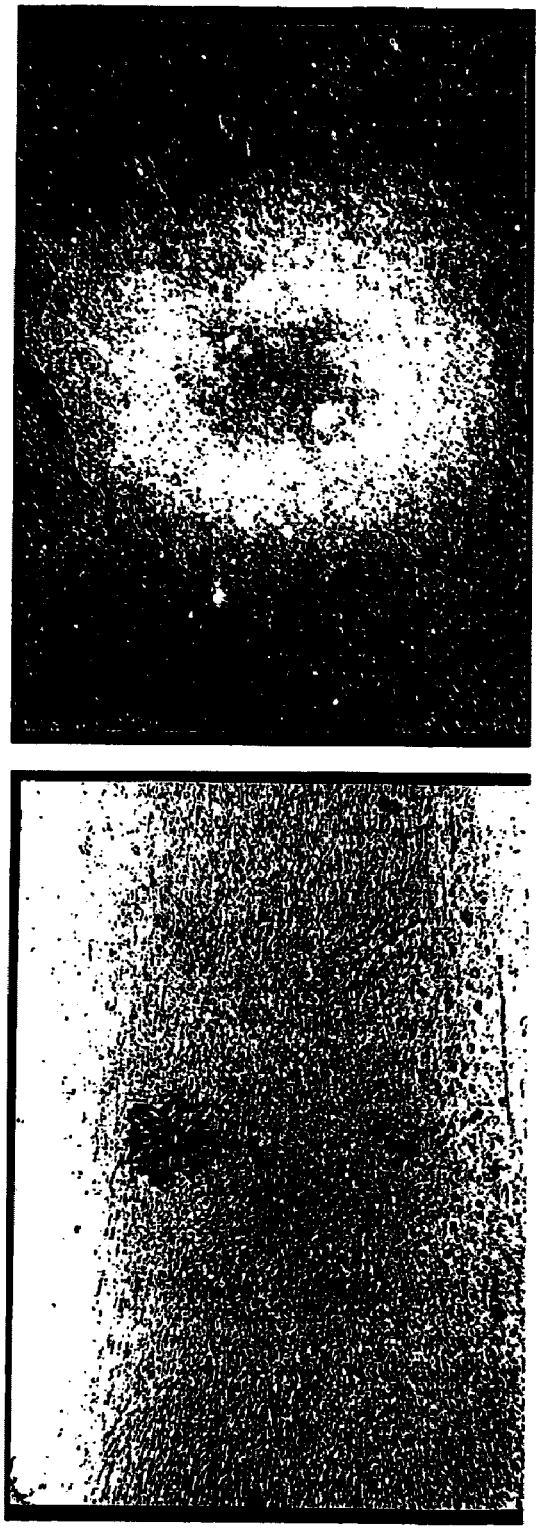
FIG. 7 shows porcine tooth tissue culture.
Figure 8:
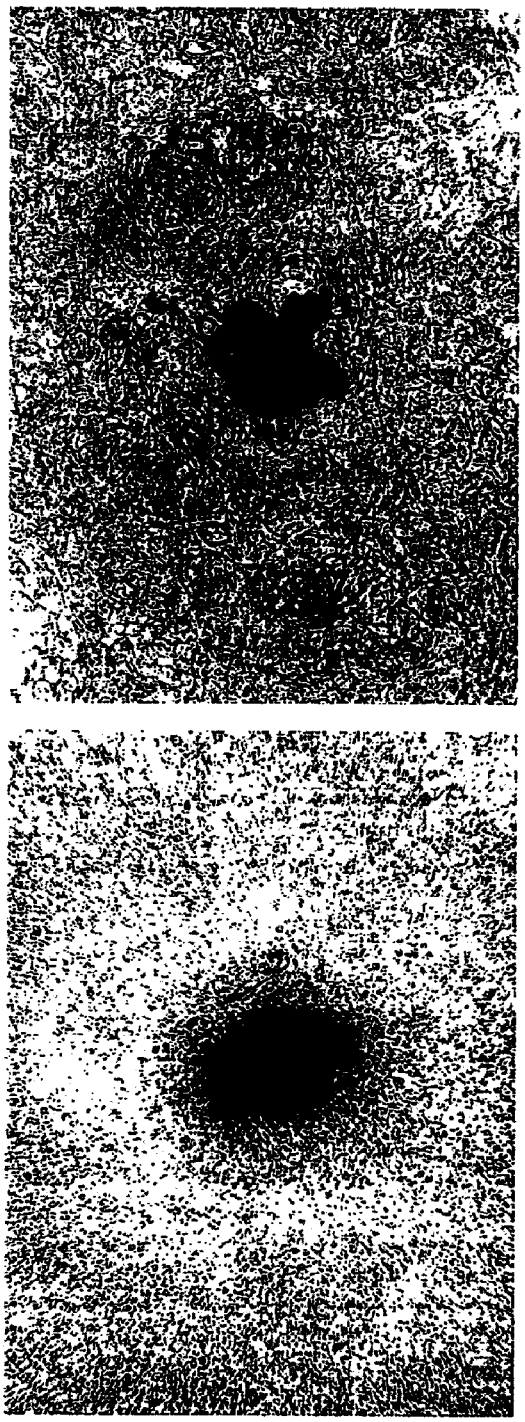
Figure 9:
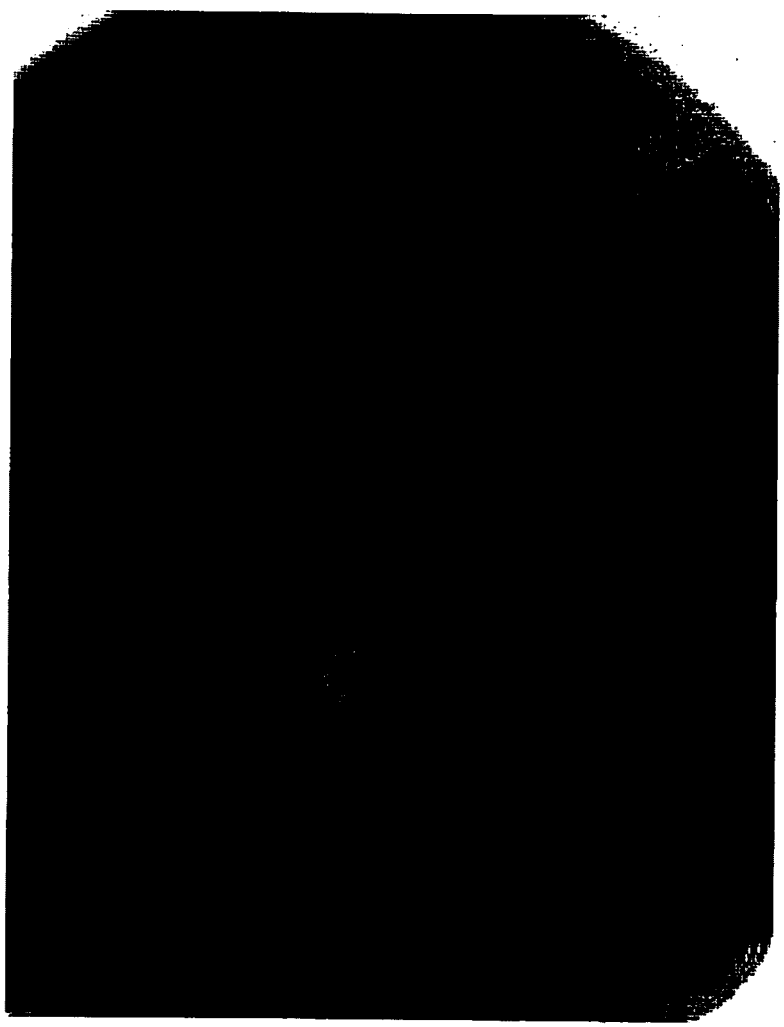
Figure 10:
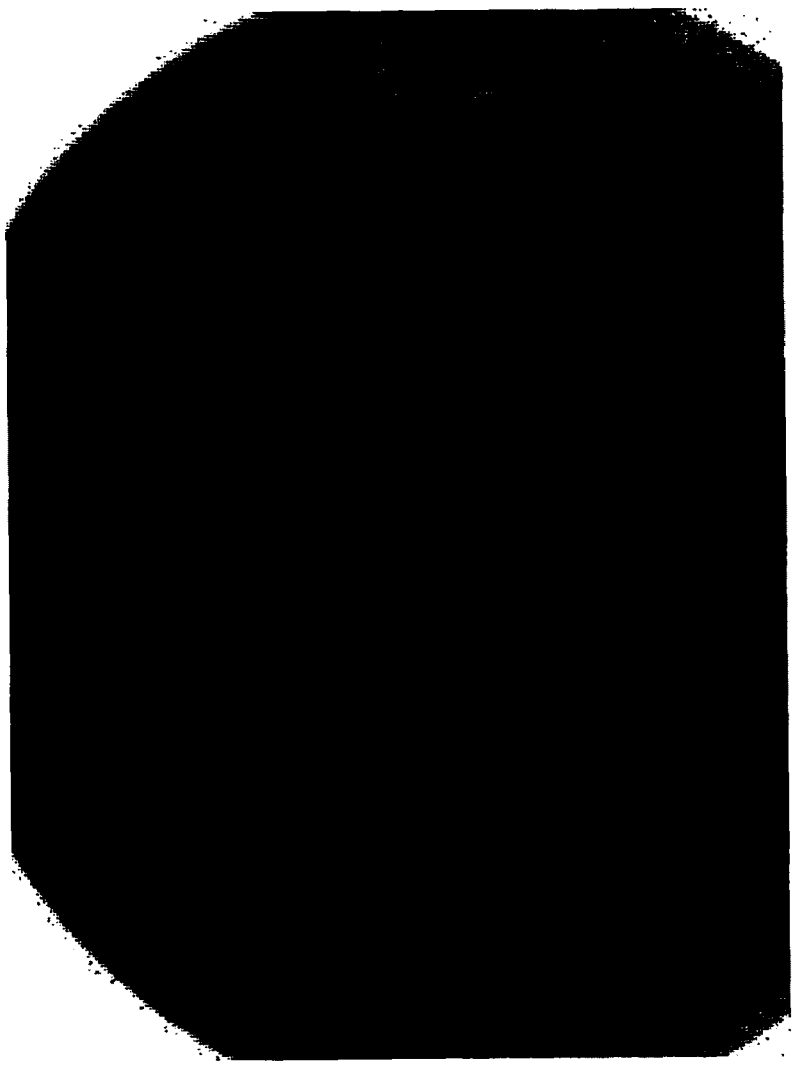
Figure 12:
Figure 13:
Figure 15:
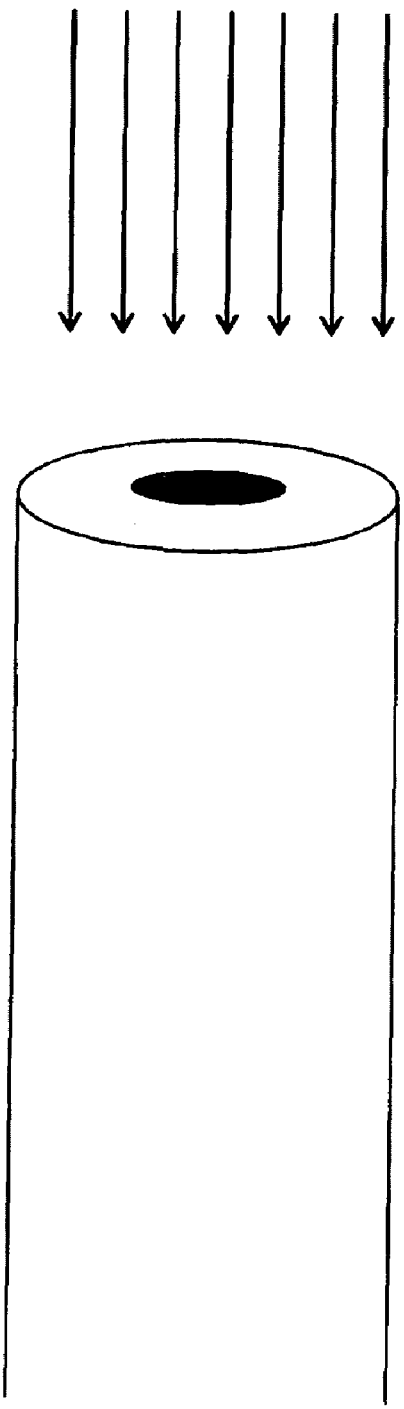
Figure 16:
Figure 17:
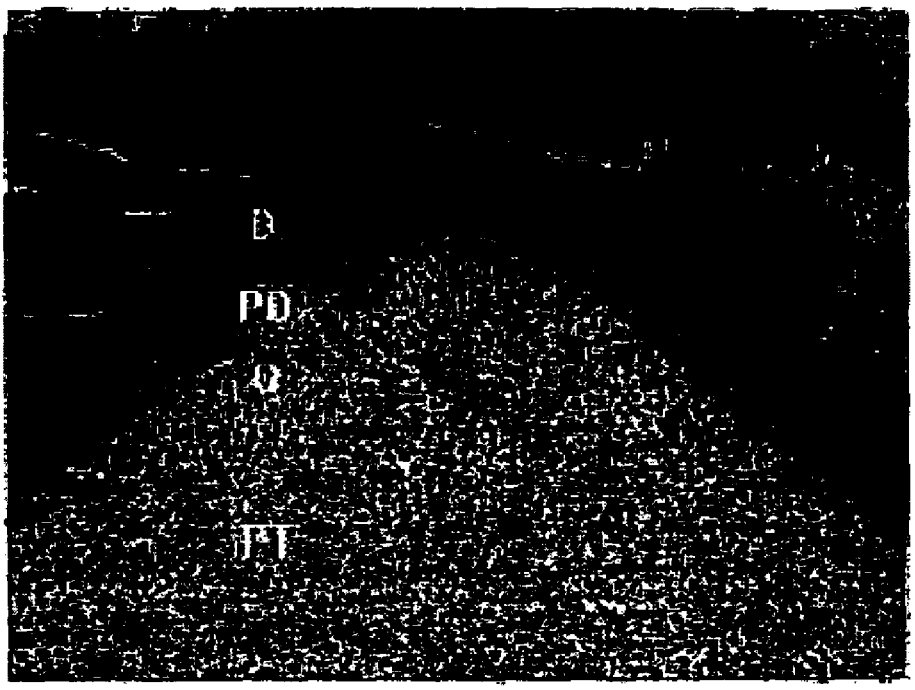
Figure 18:
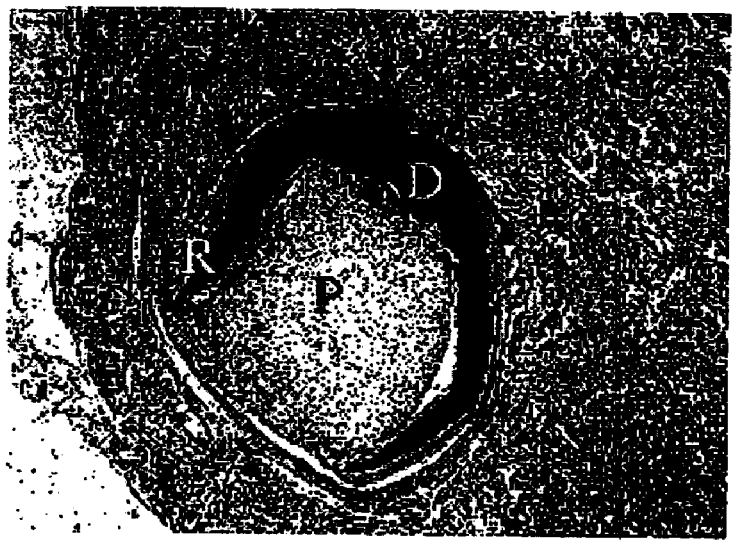
Figure 18:
Figure 19:
Figure 19:
Figure 20:
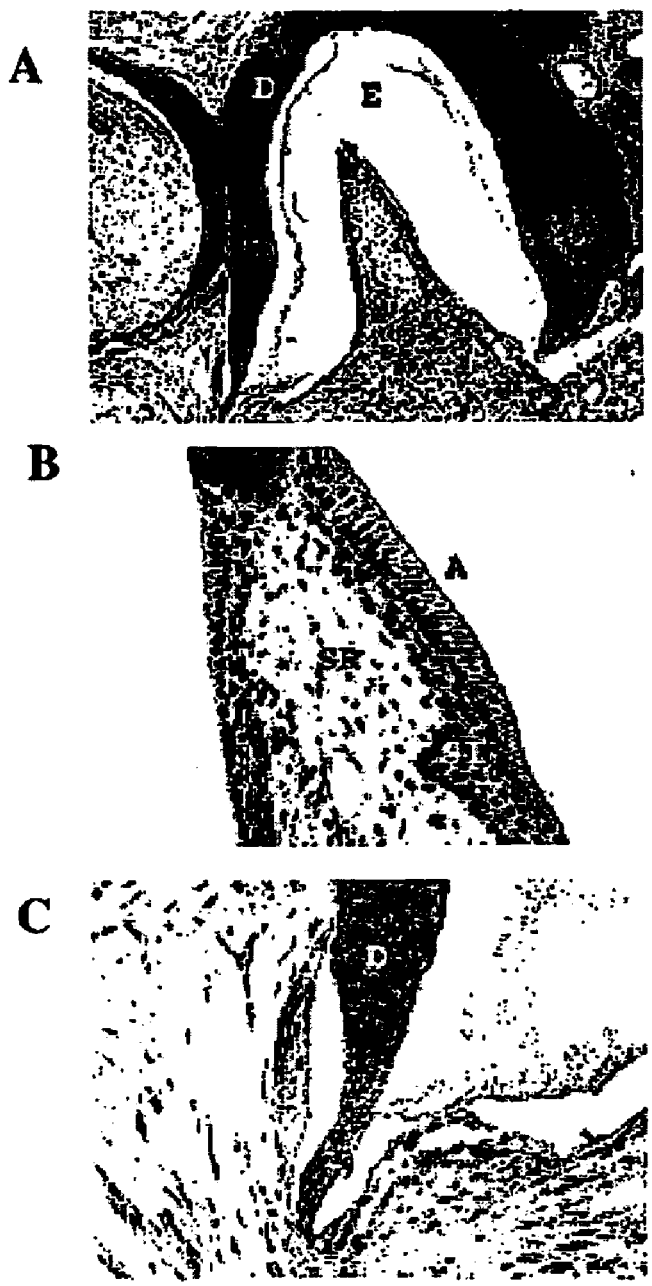
Figure 1:
Figure 1:
Figure 2:
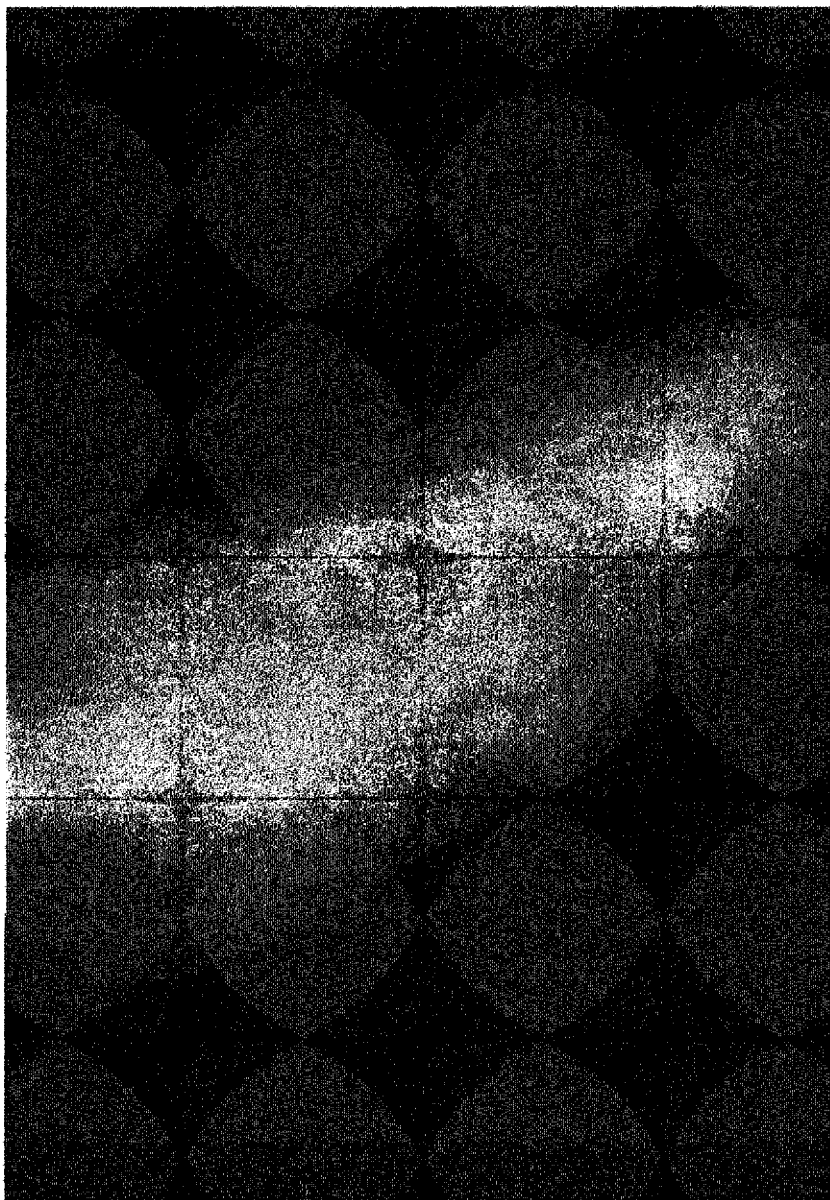
Figure 3:
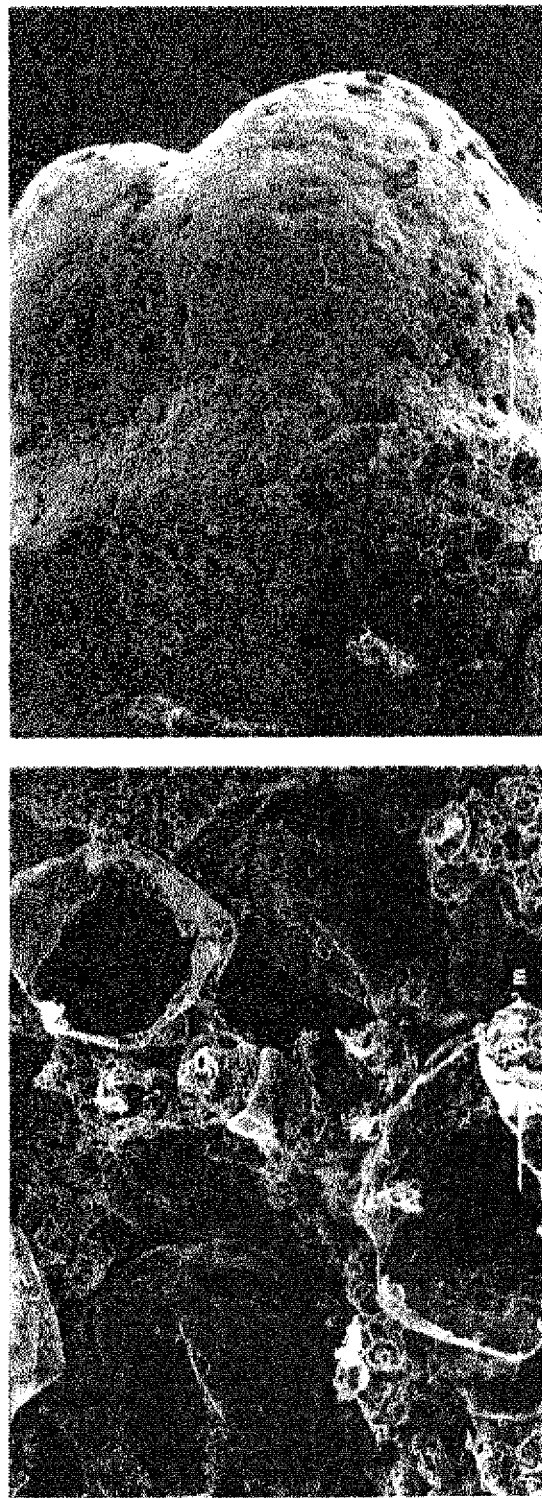
Figure 4:
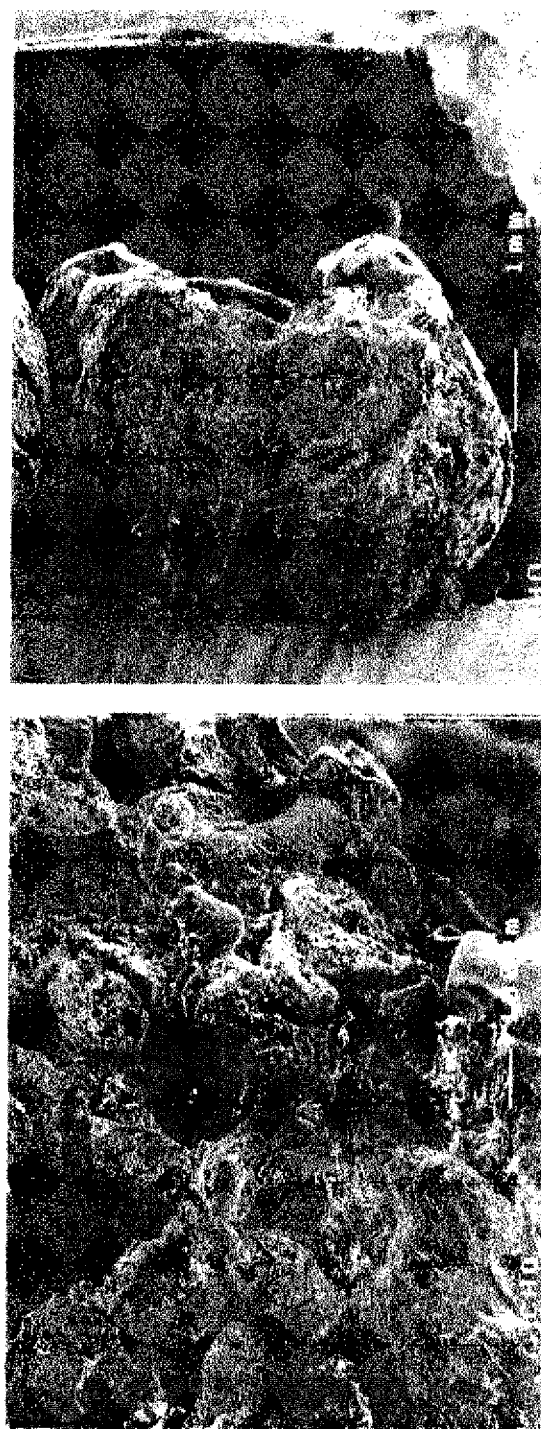
Figure 6:
Figure 7:
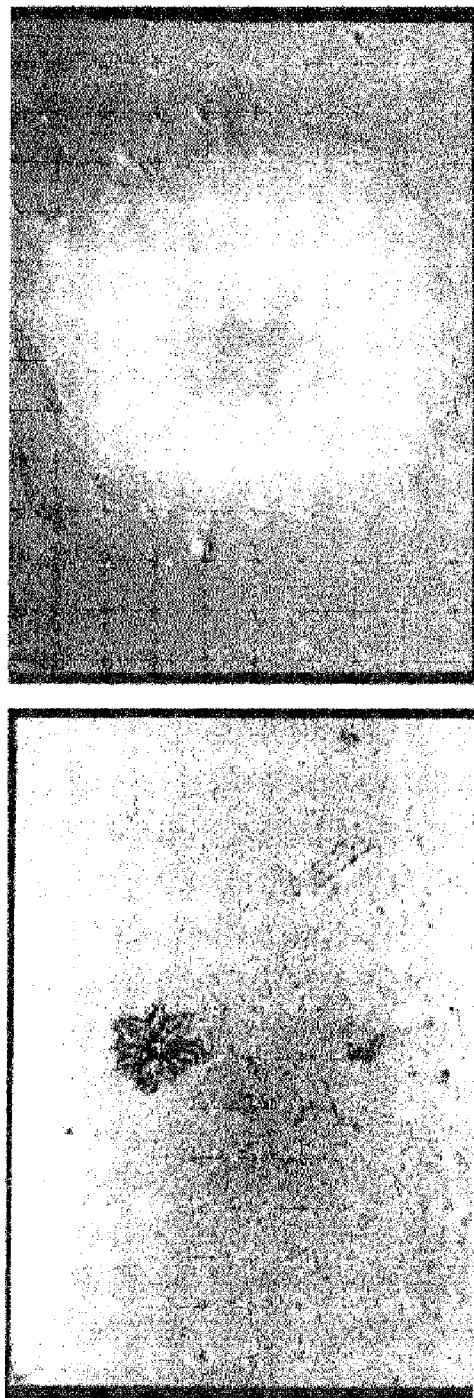
Figure 8:
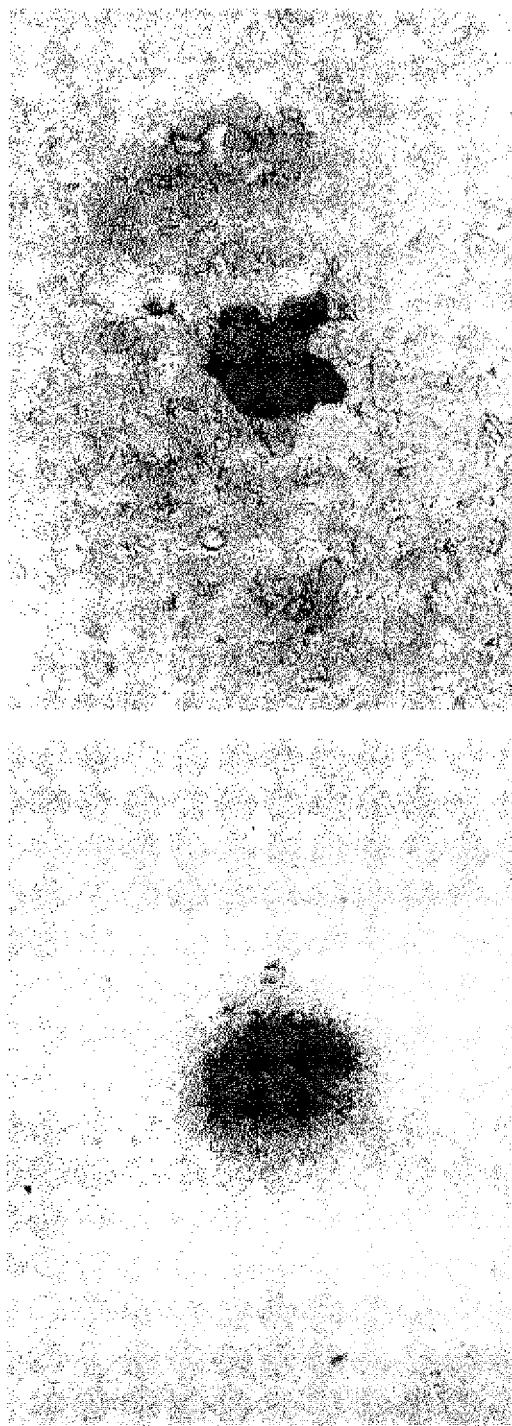
Figure 9:
Figure 10:
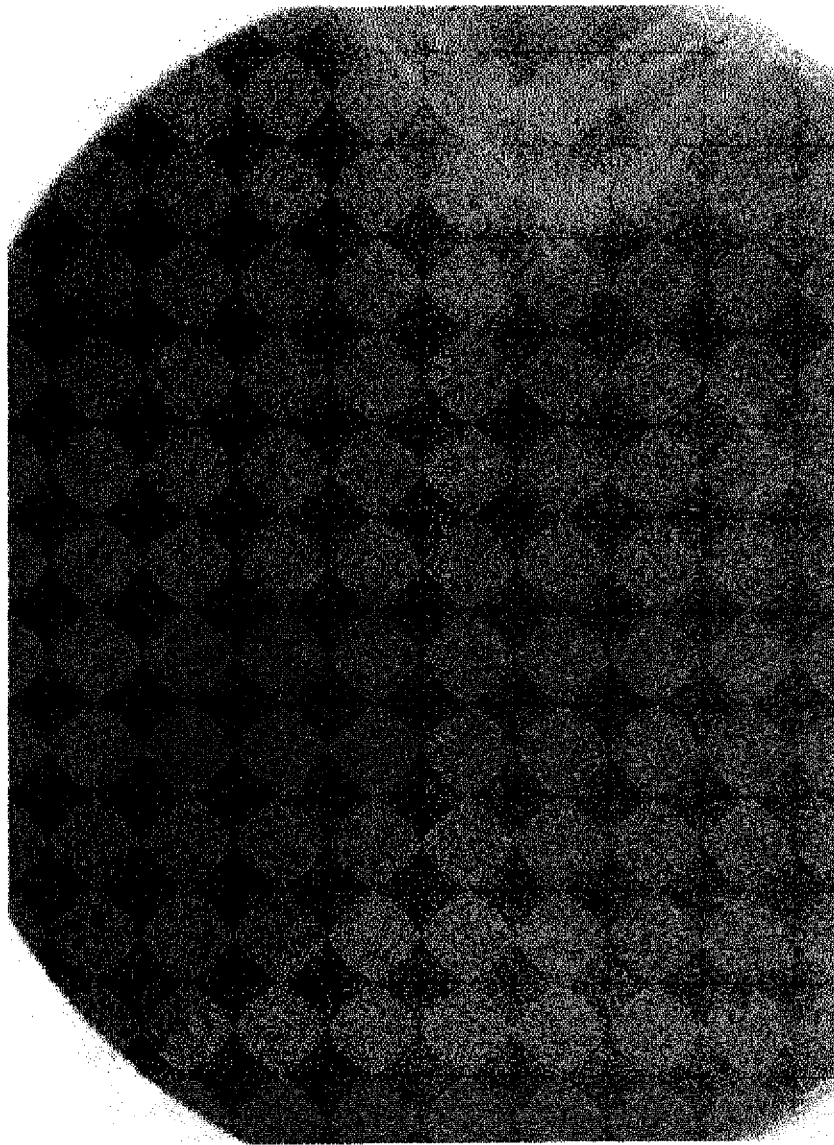
Figure 13:

Thirty week implant. Anatomy of an inverted tooth. Porcine tooth tissues were seeded onto a PLGA scaffold which was implanted into a nude rat and harvested 30-weeks later. FIGS. 20A–C show a demineralized, hemotoxylin-stained section from the implant. FIG. 20A shows a layer of dentin that surrounds a thick layer of enamel. A close-up reveals the unmistakable columnar rows of ameloblasts (A) with polarized nuclei (FIG. 20B). The cellular tissue adjacent to the ameloblasts is morphologically similar to the stratum intermedium and the remaining cellular tissue is very similar to the stellate reticulum. Thus, it appears that the three major tissue morphologies of the enamel organ are also present within this inverted tissue engineered tooth. Even more striking, was the appearance of putative cementoblasts (C) that were embedded within their own matrix (FIG. 20C).

Thus, although this is an inverted tissue-engineered tooth, this tooth appears to be developing all the necessary components of a healthy maturing tooth. We believe that this small tooth structure (approximately 2 mm in length) is inverted because not enough cells were originally seeded onto the scaffold. Previous studies demonstrate that approximately, 20–50 million cells are required per square cm for engineered tissues to conform to the shape of the scaffold and this implant had approximately 10 fold less cells than was required.

In a separate set of experiments designed to confirm the identity of the engineered tissues, we performed immunohistochemical analysis using antibodies specific for proteins present in epithelia, dentin/bone, or enamel. Immunohistochemical analysis of decalcified porcine M3 control teeth with an anti-pancytokeratin antibody resulted in staining of porcine ameloblasts and stratum intermedium cells, but no staining of the odontoblasts. The same antibody reacted relatively strongly with rat epithelial cells present in sectioned rat mandible tissue. We are evaluating engineered tooth tissues by immunohistochemical staining with the anti-pancytokeratin antibody as well as antibodies against amelogenin, osteocalcin, bone sialoprotein, and dentin sialophosphoprotein (DSPP). We are currently performing in situ hybridization analysis for the dentin-specific protein DSPP to confirm the identity of the odontoblasts and dentin tissues. These marker analyses will help identify ameloblasts, odontoblasts, and cementoblasts present in the tissue-engineered tooth tissues.

In conclusion, we have demonstrated successful engineering of recognizable teeth, using biodegradable polymer scaffolds seeded with porcine third molar tooth cells. The teeth form dentin from cells appearing to be odontoblasts, have a well defined pulp chamber, possess putative Hertwig's root sheath epithelial, possess putative cementoblasts, and have a morphologically correct enamel organ consisting of stellate reticulum, stratum intermedium, and ameloblasts, and have what appears to be fully formed dental enamel.

References

Annual Industry Report, *Implant Dentistry* 9(3): 192–194, 2000.

Baba T, Terashima T, Oida S, Sasaki S. (1996). Determination of enamel protein synthesized by recombinant mouse molar tooth germs in organ culture. Archives of Oral Biology 41:215–9.

Backman, B. and A. K. Hohm. Amelogenesis imperfecta: prevalence and incidence in a northern Swedish county. *Community Dent Oral Epidemiol*, 14(1):43–7, 1986.

Choi R S, Riegler M, Pothoulakis C, Kim B S, Mooney D, Vacanti M, et al. (1998). Studies of brush border enzymes, basement membrane components, and electrophysiology of tissue-engineered neointestine. J Pediatr Surg 33:991–6; discussion 996–7.

Choi R. S. and J. P. Vacanti Preliminary studies of tissue-engineered intestine using isolated epithelial organoid units on tubular synthetic biodegradable scaffolds. *Transplant Proc*. 29(1–2):848–51, 1997.

Chosack, A., et al. Amelogenesis imperfecta among Israeli Jews and the description of a new type of local hypoplastic autosomal recessive amelogenesis imperfecta. *Oral Surg Oral Med Oral Pathol*, 47:148–156, 1979.

DenBesten, P. K. et al. Eur. J. Oral Sci. 107: 276–281, 1999.

Dummer, P. M., A. Kingdon, and R. Kingdon. Prevalence and distribution by tooth type and surface of developmental defects of dental enamel in a group of 15- to 16-year-old children in South Wales. *Community Dent Health,* 7(4): 369–377, 1990.

Gronthos, S. et al., Proc. Natl. Acad. Sci. USA 97(25): 13625–13630, 2000.

Haffen K, Kedinger M, Simon-Assmann P. (1987). Mesenchyme-dependent differentiation of epithelial progenitor cells in the gut. [Review] [48 refs]. J Pediatr Gastroenterol Nutr 6:14–23.

Isogai N, Landis W, Kim T H, Gerstenfeld L C, Upton J, and Vacanti J P. Formation of phalanges and small joints by tissue-engineering. J Bone Joint Surg Am 1999;81(3):306–16.

Kaihara S, Kim S S, Benvenuto M, Choi R, Kim B S, Mooney D, Tanaka K, and Vacanti J P. Successful anastomosis between tissue-engineered intestine and native small bowel. Transplantation 1999;67(2):241–5.

Kim S. S. and J. P. Vacanti. The current status of tissue engineering as potential therapy. *Semin Pediatr Surg.* 8(3): 119–23, 1999.

Stevens A, Lowe L., Bancroft J. D. *Theory and practice of histological techniques,* A. Stevens and J. D. Bancroft, Editors. Churchill Livingstone. New York. p. 333–335.

Thesleff I, Partanen A M, Vainio S. (1991).Epithelial-mesenchymal interactions in tooth morphogenesis: the roles of extracellular matrix, growth factors, and cell surface receptors. J Craniofac Genet Dev Biol 11:229–37.

Witkop Jr., C. J. and J. J. Sauk Jr. *Heritable defects of enamel,* in *Oral facial genetics,* R. E. Stewart and G. H. Prescott, Editors. C. V. Mosby Co.: St. Louis. p. 151–226, 1976.

Witkop Jr., C. J. and S. Rao. Inherited defects in tooth structure. *Birth Defects,* 7:153–184, 1971.

Xiao, S., et al. Dentinogenesis imperfecta 1 with or without progressive hearing loss is associated with distinct mutations in DSPP, *Nat Genet,* 27:201–204, 2001.

Zang, X., et al. DSPP mutation in dentinogenesis imperfecta Shields type II, *Nat Genet,* 27:151–152, 2001.

What is claimed is:

1. A method to make new tooth tissue comprising, applying tooth germ cells onto a biodegradable polymer scaffold and allowing the tooth germ cells to develop into a tooth for implantation, wherein the tooth germ cells comprise cells from an enamel organ and a pulp organ.

2. The method of generating tooth tissue of claim 1, wherein the tooth germ cells are mammalian.

3. The method of generating tooth tissue of claim 1, wherein the tooth germ cells are porcine.

4. A method of generating tooth tissue comprising, applying tooth germ cells onto a biodegradable polymer scaffold and allowing the tooth germ cells to develop into a tooth for implantation, wherein the tooth germ cells comprise cells dissociated from an enamel organ, a pulp organ, and from tissue cultured cells derived from tooth tissues.

5. A method of generating tooth tissue comprising, applying tooth germ cells onto a biodegradable polymer scaffold and allowing the tooth germ cells to develop into a tooth for implantation, wherein the scaffold is implanted into an omentum of a host animal.

6. The method of generating tooth tissue of claim 5, wherein the scaffold is implanted into the omentum of a rat.

7. A The method of generating tooth tissue comprising, forming a biodegradable polymer scaffold, applying tooth germ cells onto the biodegradable polymer scaffold, and implanting the scaffold into a host animal, wherein the tooth germ cells comprise cells dissociated from an enamel organ and a pulp organ.

8. The method of generating tooth tissue of claim 7, wherein the tooth germ cells are mammalian.

9. The method of generating tooth tissue of claim 7, wherein the tooth germ cells are porcine.

10. The method of generating tooth tissue of claim 7, wherein the tooth germ cells comprise cells dissociated from an enamel organ, a pulp organ, and from tissue cultured cells derived from tooth tissues.

11. The method of generating tooth tissue of claim 7, wherein the scaffold is implanted into an omentum of a host animal.

12. The method of generating tooth tissue of claim 11, wherein the scaffold is implanted into the omentum of a rat.

13. A method of generating tooth tissue comprising preparing a tooth mold in the shape of a human tooth, forming a biodegradable polymer scaffold in the tooth mold, applying tooth germ cells onto the biodegradable polymer scaffold, and implanting the scaffold into an omentum of a host animal.

14. The method of generating tooth tissue of claim 13, wherein the tooth germ cells comprise cells from an enamel organ and a pulp organ.

15. The method of generating tooth tissue of claim 13, wherein the tooth germ cells are mammalian.

16. The method of generating tooth tissue of claim 13, wherein the tooth germ cells are porcine.

17. The method of generating tooth tissue of claim 13, wherein the tooth germ cells comprise cells dissociated from an enamel organ, a pulp organ, and from tissue cultured cells derived from tooth tissues.

18. The method of generating tooth tissue of claim 13, wherein the scaffold is implanted into the omentum of a rat.

19. The method of generating tooth tissue of claim 13, wherein the tooth germ cells are applied to the biodegradable polymer scaffold with between about 20 to 50 million cells per square inch of scaffold.

20. The method of generating tooth tissue of claim 13, wherein the biodegradable polymer scaffold is selected from the group consisting of poly(lactide), poly(glycolide), and poly(L-lactide-co-glycolide).

21. The method of generating tooth tissue of claim 13, wherein the tooth germ cells are allowed to attach to the scaffold for at least one hour prior to implanting.

22. The method of generating tooth tissue of claim 13, wherein the biodegradable polymer scaffold is coated in collagen prior to applying.

23. The method of generating tooth tissue of claim 1, wherein the tooth germ cells comprise cells dissociated from an enamel organ, a pulp organ, and from tissue cultured cells derived from tooth tissues.

24. The method of generating tooth tissue of claim 1, wherein the biodegradable polymer scaffold is in the shape of a human tooth.

25. The method of generating tooth tissue of claim 1, wherein the biodegradable polymer scaffold is in the shape of a tooth.

26. The method of generating tooth tissue of claim 1, wherein the scaffold is implanted into an omentum of a host animal.

27. The method of generating tooth tissue of claim 1, wherein the scaffold is implanted into the omentum of a rat.

28. The method of generating tooth tissue of claim 1, wherein the tooth germ cells are applied to the biodegradable polymer scaffold with between about 20 to 50 million cells per square inch of scaffold.

29. The method of generating tooth tissue of claim 1, wherein the biodegradable polymer scaffold is selected from the group consisting of poly(lactide), poly(glycolide), and poly(L-lactide-co-glycolide).

30. The method of generating tooth tissue of claim 1, wherein the tooth germ cells are allowed to attach to the scaffold for at least one hour prior to implanting.

31. The method of generating tooth tissue of claim 1, wherein the biodegradable polymer scaffold is coated in collagen prior to applying.

32. The method of generating tooth tissue of claim 4, further comprising forming a tooth mold, wherein the biodegradable polymer scaffold is formed in the tooth mold.

33. The method of generating tooth tissue of claim 4, wherein the biodegradable polymer scaffold is in the shape of a tooth.

34. The method of generating tooth tissue of claim 4, wherein the biodegradable polymer scaffold is in the shape of a human tooth.

35. The method of generating tooth tissue of claim 4, wherein the tooth germ cells are mammalian or porcine.

36. The method of generating tooth tissue of claim 4, wherein the scaffold is implanted into an omentum of a host animal.

37. The method of generating tooth tissue of claim 4, wherein the scaffold is implanted into the omentum of a rat.

38. The method of generating tooth tissue of claim 4, wherein the tooth germ cells are applied to the biodegradable polymer scaffold with between about 20 to 50 million cells per square inch of scaffold.

39. The method of generating tooth tissue of claim 4, wherein the biodegradable polymer scaffold is selected from the group consisting of poly(lactide), poly(glycolide), and poly(L-lactide-co-glycolide).

40. The method of generating tooth tissue of claim 4, wherein the tooth germ cells are allowed to attach to the scaffold for at least one hour prior to implanting.

41. The method of generating tooth tissue of claim 4, wherein the biodegradable polymer scaffold is coated in collagen prior to applying.

42. The method of generating tooth tissue of claim 5, further comprising forming a tooth mold, wherein the biodegradable polymer scaffold is formed in the tooth mold.

43. The method of generating tooth tissue of claim 5, wherein the biodegradable polymer scaffold is in the shape of a tooth.

44. The method of generating tooth tissue of claim 5, wherein the biodegradable polymer scaffold is in the shape of a human tooth.

45. The method of generating tooth tissue of claim 5, wherein the tooth germ cells are mammalian.

46. The method of generating tooth tissue of claim 5, wherein the tooth germ cells are porcine.

47. The method of generating tooth tissue of claim 5, wherein the scaffold is implanted into the omentum of a rat.

48. The method of generating tooth tissue of claim 5, wherein the tooth germ cells are applied to the biodegradable polymer scaffold with between about 20 to 50 million cells per square inch of scaffold.

49. The method of generating tooth tissue of claim 5, wherein the biodegradable polymer scaffold is selected from the group consisting of poly(lactide), poly(glycolide), and poly(L-lactide-co-glycolide).

50. The method of generating tooth tissue of claim 5, wherein the tooth germ cells are allowed to attach to the scaffold for at least one hour prior to implanting.

51. The method of generating tooth tissue of claim 5, wherein the biodegradable polymer scaffold is coated in collagen prior to applying.

52. The method of generating tooth tissue of claim 7, further comprising preparing a tooth mold wherein the biodegradable polymer scaffold is formed in the tooth mold.

53. The method of generating tooth tissue of claim 7, wherein the biodegradable polymer scaffold is in the shape of a tooth.

54. The method of generating tooth tissue of claim 7, wherein the biodegradable polymer scaffold is in the shape of a human tooth.

* * * * *

UNITED STATES PATENT AND TRADEMARK OFFICE
CERTIFICATE OF CORRECTION

| | |
|---|---|
| PATENT NO. | : 6,899,915 B2 |
| APPLICATION NO. | : 09/997734 |
| DATED | : May 31, 2005 |
| INVENTOR(S) | : Dunn |

It is certified that error appears in the above-identified patent and that said Letters Patent is hereby corrected as shown below:

Delete Title page illustrating figure, and substitute new Title page illustrating figure attached.

Delete drawing sheets 1-20, and substitute drawing sheets 1-20, with the attached sheets.

Signed and Sealed this

Eighth Day of August, 2006

JON W. DUDAS
*Director of the United States Patent and Trademark Office*

(12) United States Patent
Yelick et al.

(10) Patent No.: US 6,899,915 B2
(45) Date of Patent: May 31, 2005

(54) METHODS AND COMPOSITIONS FOR CULTURING A BIOLOGICAL TOOTH

(75) Inventors: Pamela C. Yelick, Concord, MA (US); John D. Bartlett, Acton, MA (US); Joseph P. Vacanti, Winchester, MA (US); Bjorn R. Olsen, Milton, MA (US); Phillip Stashenko, Medfield, MA (US)

(73) Assignees: President and Fellows of Harvard College, Cambridge, MA (US); General Hospital Corporation, Boston, MA (US); Forsyth Dental Infirmary for Children, Inc., Boston, MA (US)

( * ) Notice: Subject to any disclaimer, the term of this patent is extended or adjusted under 35 U.S.C. 154(b) by 0 days.

(21) Appl. No.: 09/997,734

(22) Filed: Nov. 29, 2001

(65) Prior Publication Data

US 2002/0119180 A1 Aug. 29, 2002

Related U.S. Application Data

(60) Provisional application No. 60/253,891, filed on Nov. 29, 2000.

(51) Int. Cl.[7] ................................................ A61C 13/08
(52) U.S. Cl. ................... 427/2.26; 433/202.1; 433/204; 264/19; 523/115
(58) Field of Search ...................... 427/2.26, 2.27; 433/202.1, 204, 215, 223; 264/19; 523/115; 521/50, 51, 55; 514/21; 424/435; 623/23.58, 23.72, 23.75

(56) References Cited

U.S. PATENT DOCUMENTS

| 5,098,891 | A | * | 3/1992 | Hammarstrom et al. | 514/21 |
| 5,418,221 | A | * | 5/1995 | Hammarstrom et al. | 514/21 |
| 5,863,297 | A | * | 1/1999 | Walter et al. | 623/17.18 |
| 5,885,829 | A | * | 3/1999 | Mooney et al. | 435/325 |
| 6,488,503 | B1 | * | 12/2002 | Lichkus et al. | 433/202.1 |
| 2002/0022883 | A1 | * | 2/2002 | Burg | 623/8 |
| 2002/0192198 | A1 | * | 12/2002 | Elia | 424/93.21 |

OTHER PUBLICATIONS

"Annual Industry Report," *Implant Dentistry*, 9(3):192–194 (2000).

Baba et al., "Determination of enamel protein synthesized by recombined mouse molar tooth germs in organ culture," *Archives of Oral Biology* 41:215–219 (1996).

Backman et al., "Amelogenesis imperfecta: prevalence and incidence in a northern Swedish country," *Community Dent Oral Epidemiol*, 14(1):43–47 (1986).

Choi et al., "Studies of brush border enzymes, basement membrane components, and electrophysiology of tissue-engineered neointestine," *J. Pediatr. Surg.* 33:991–6; discussion 996–997 (1998).

(Continued)

*Primary Examiner*—James J. Seidleck
*Assistant Examiner*—Melanie Bissett
(74) *Attorney, Agent, or Firm*—Banner & Witcoff, Ltd.

(57) ABSTRACT

Tooth tissues include the pulp mesenchyme that forms the dentin and an epithelium that is responsible for enamel formation. Cells from these tissues were obtained from porcine third molars and were seeded onto a biodegradable scaffold composed of a polyglycolic acid—polylactic acid copolymer. Cell polymer constructs were then surgically implanted into the omentum of athymic nude rats so that the constructs would have a blood supply and these tissues were allowed to develop inside the rats. Infrequently, columnar epithelial cells were observed as a single layer on the outside of the dentin-like matrix similar to the actual arrangement of ameloblasts over dentin during early tooth development. Developing tooth tissues derived from such cell polymer constructs could eventually be surgically implanted into the gum of an edentulous recipient where the construct would receive a blood supply and develop to maturity, providing the recipient with a biological tooth replacement.

54 Claims, 20 Drawing Sheets

Tooth Scaffolds

PGA + PLLA

Tooth Scaffolds  PGA + PLLA

Porcine Tooth Tissue Culture

Tissue Culture-Von Kossa Stain

Rat Radiographs - Human Tooth

Rat Radiographs - Implant, 7.5 weeks

Figure 11:
FIGS. 11 and 12 show dissection of tissue.

Fig. 11 — Dissection of Tissue

Dissection of Tooth Tissue
7.5 weeks

Dissected Tooth Tissue - 7.5 Weeks

Figure 14:
Figure 15:
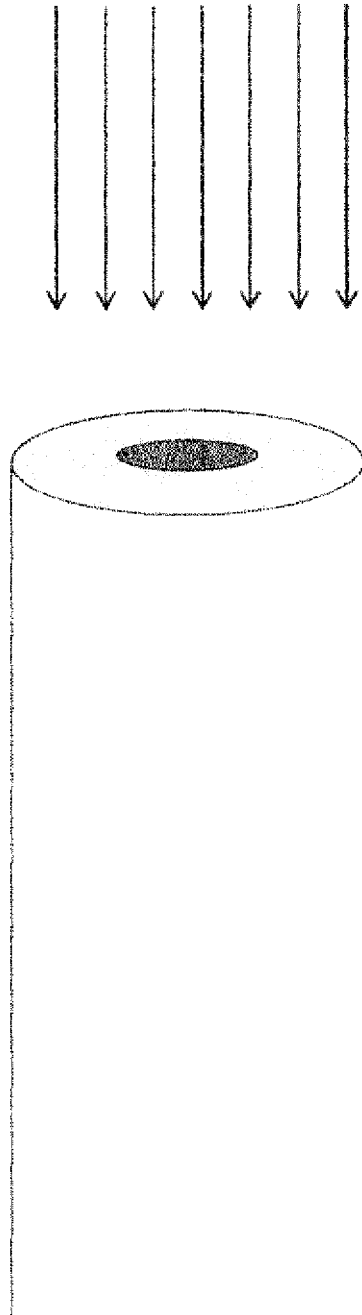
Figure 16:
Figure 17:
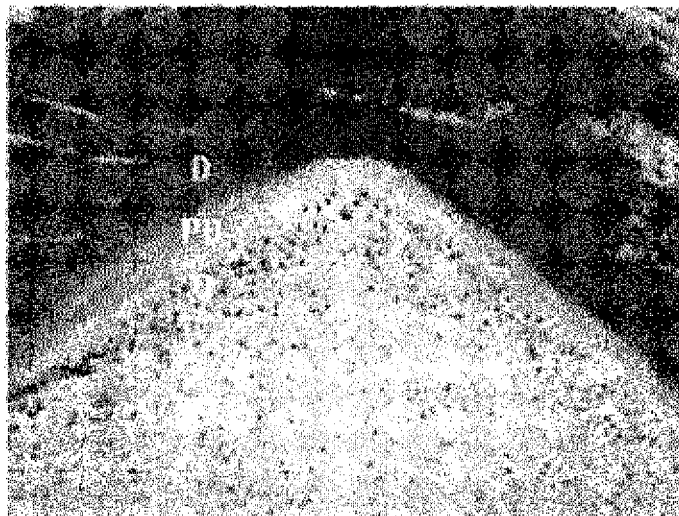
Figure 18:
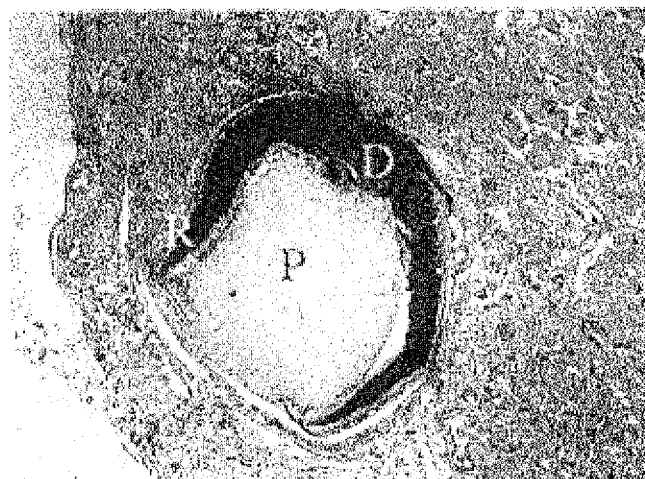
Figure 18:
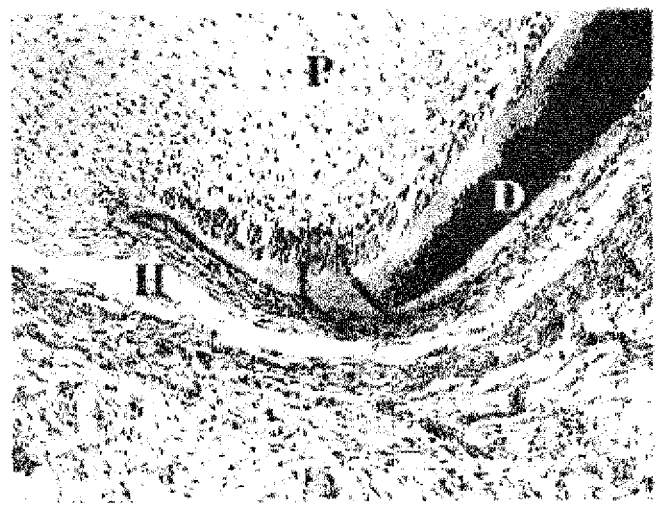
Figure 19:
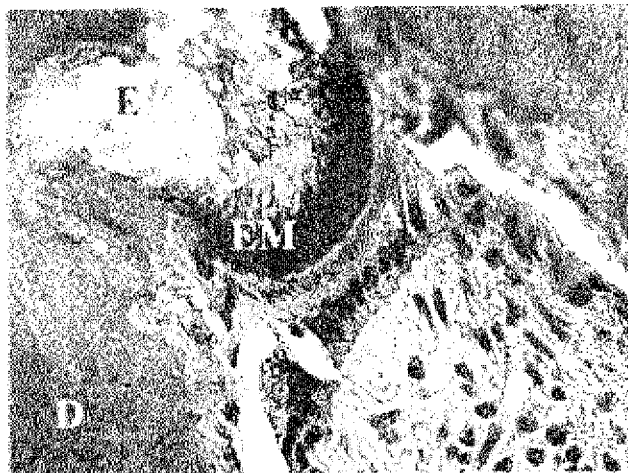
Figure 19:
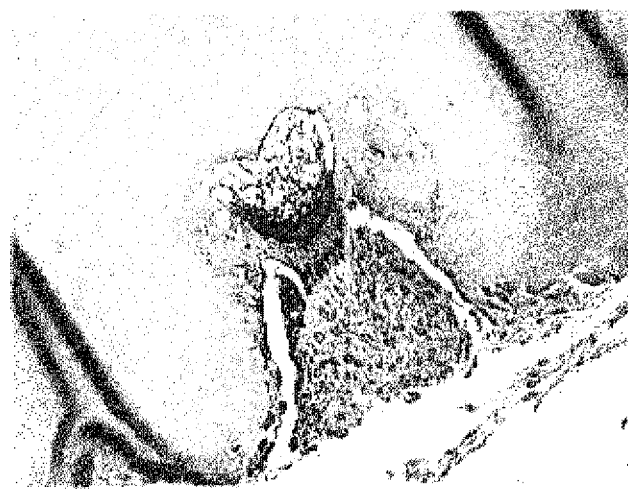
Figure 20:
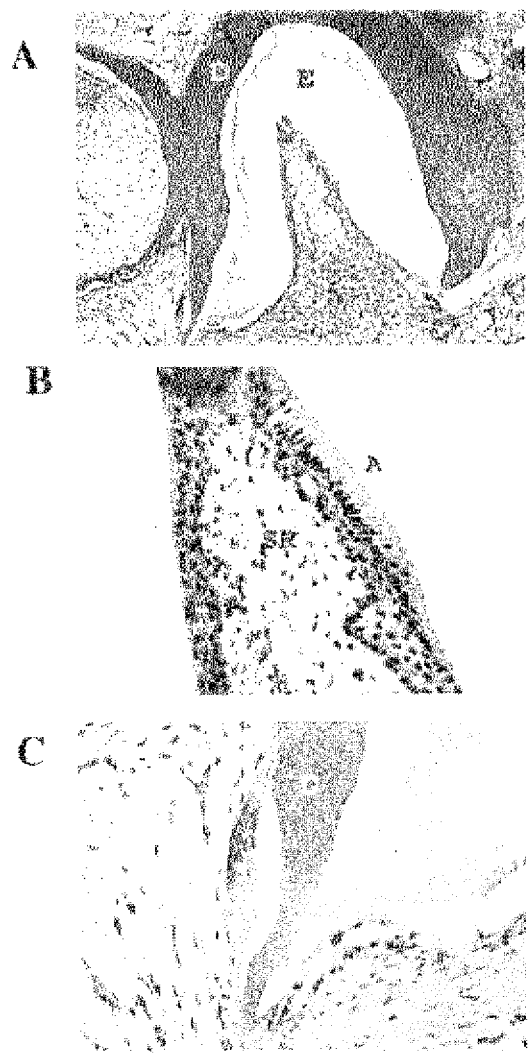
Figure 1:
Figure 1:
Figure 2:
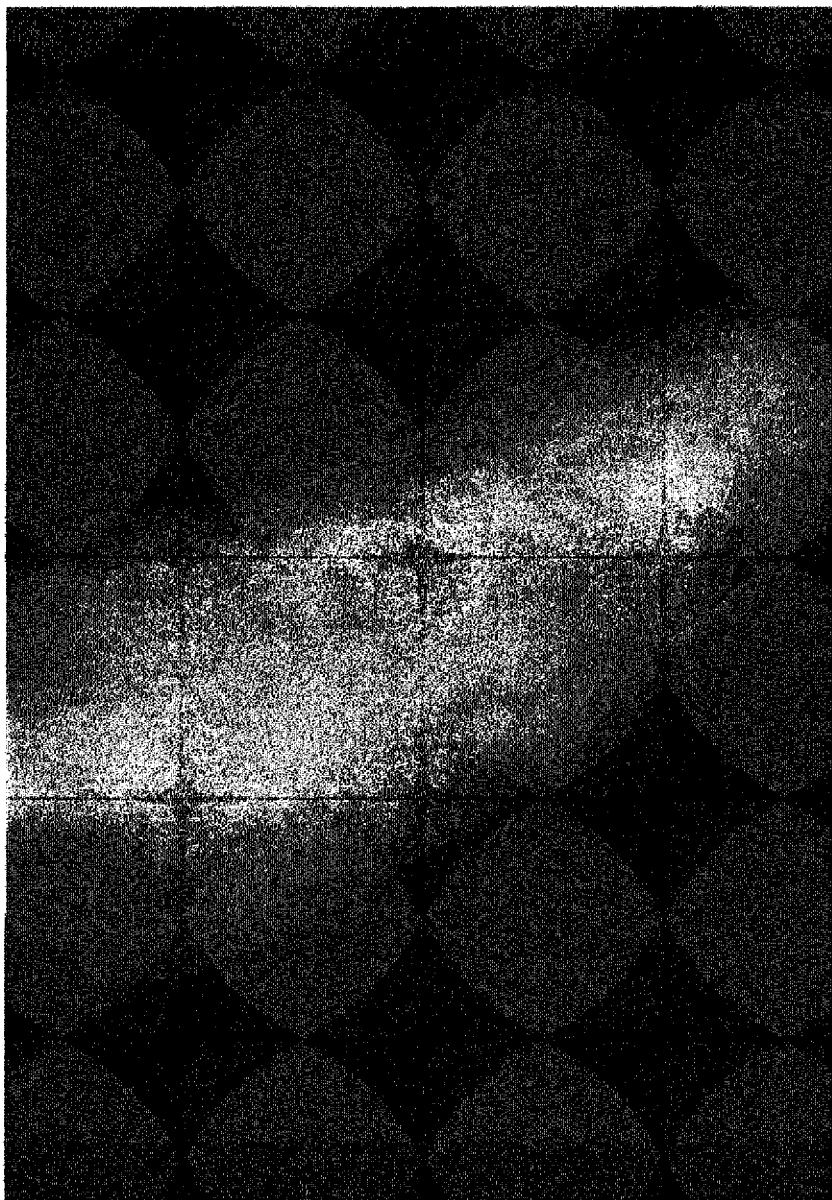
Figure 3:
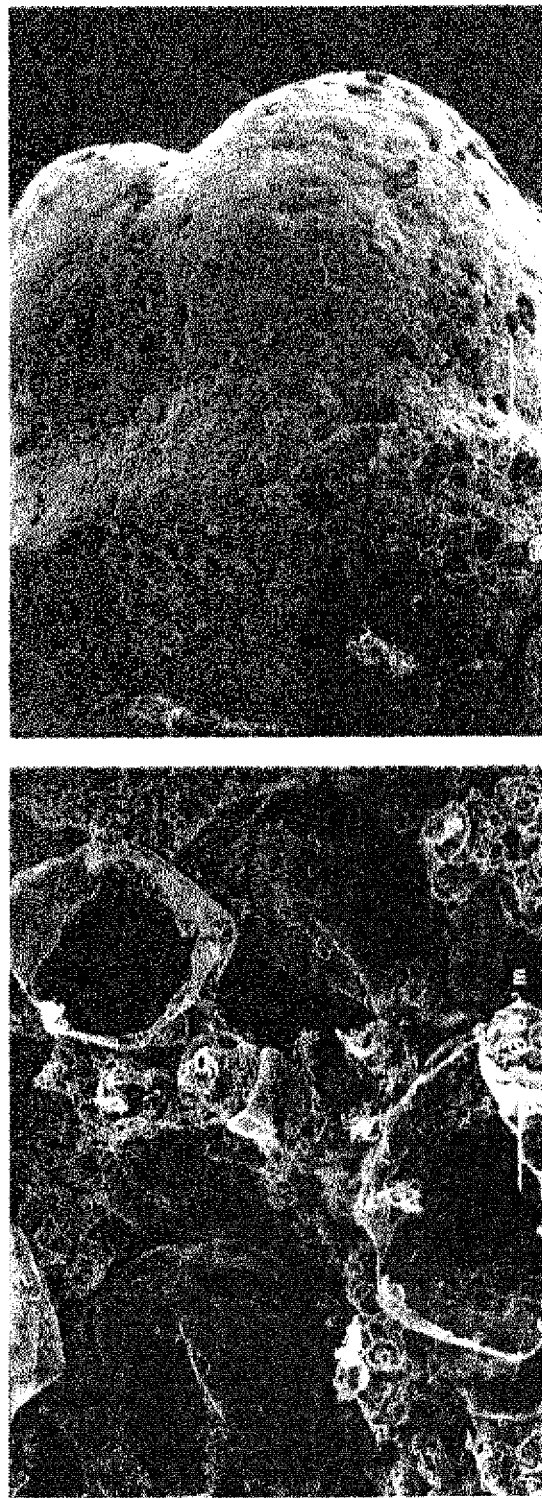
Figure 4:
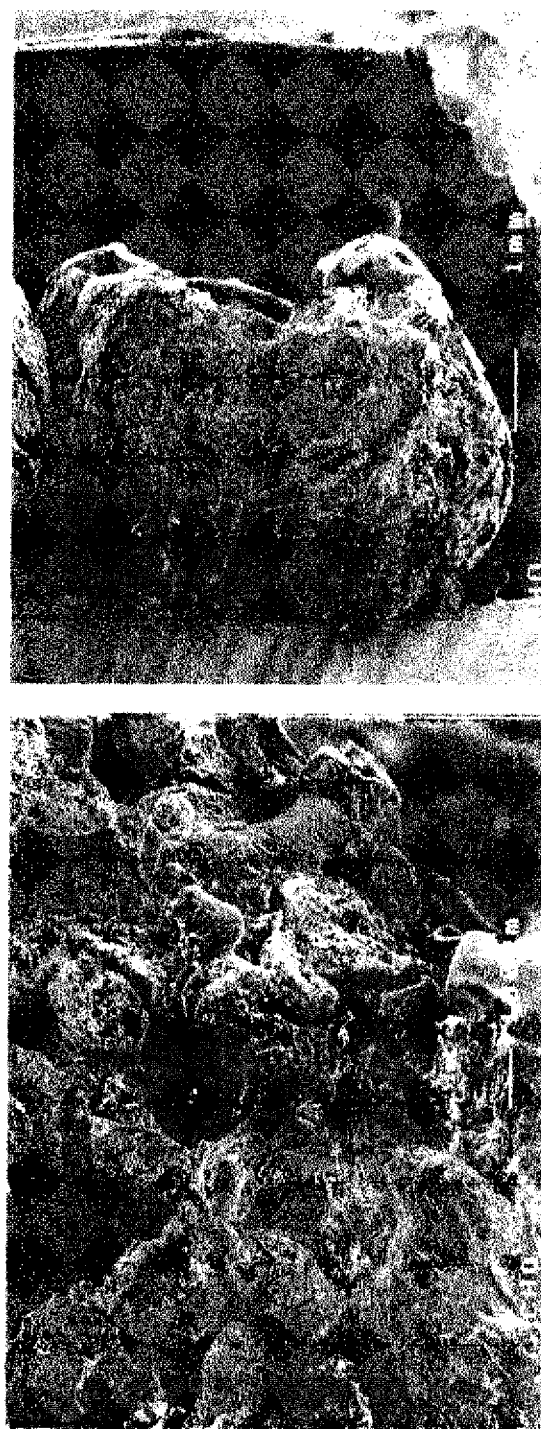
Figure 6:
Figure 7:
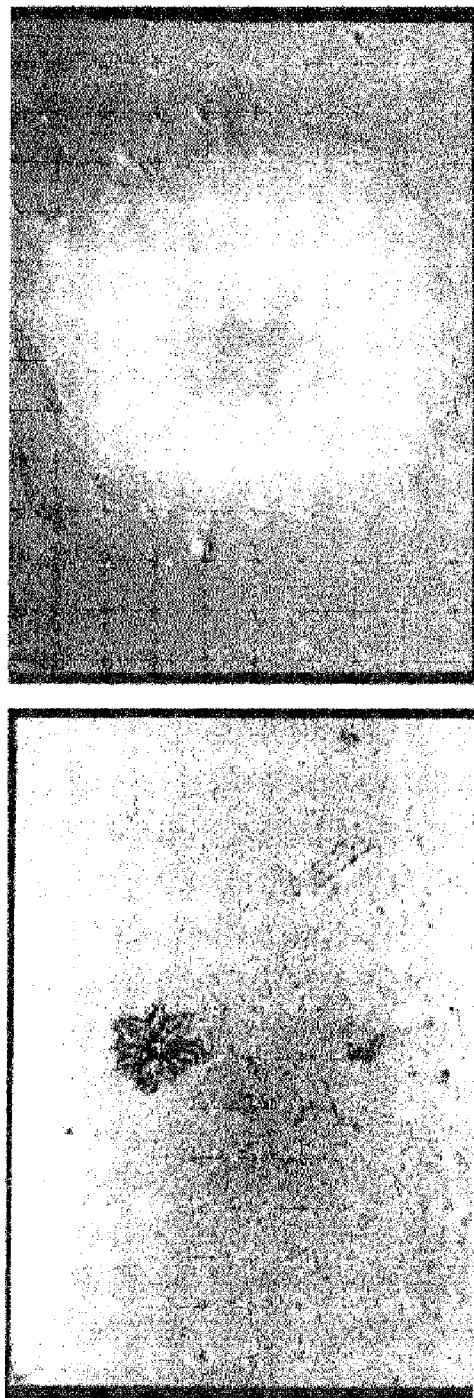
Figure 8:
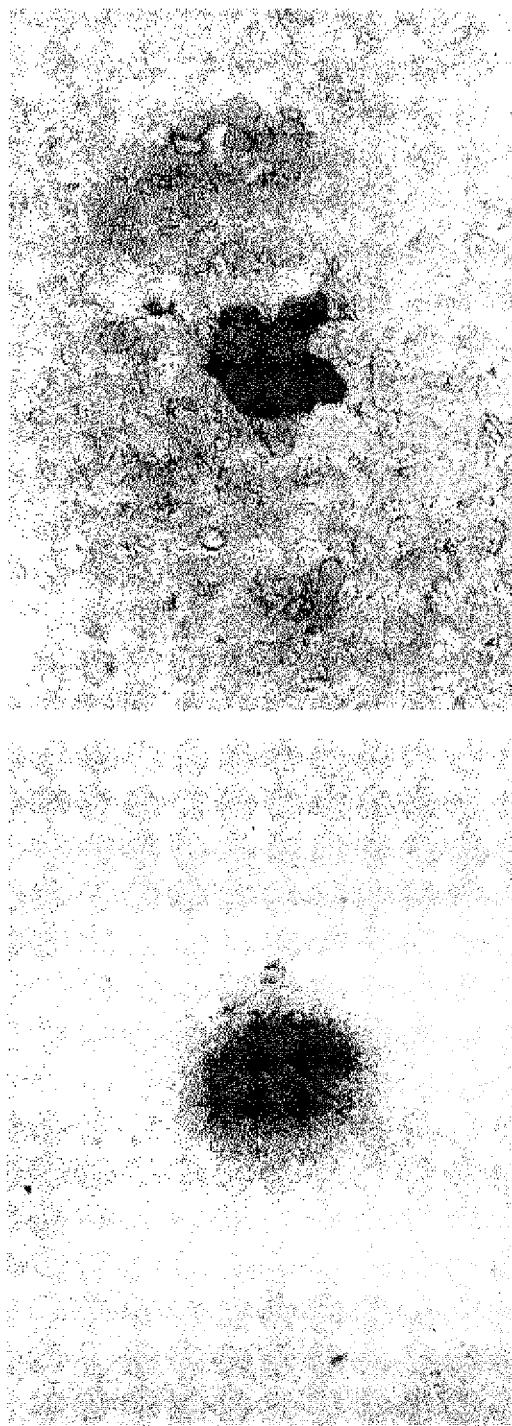
Figure 10:
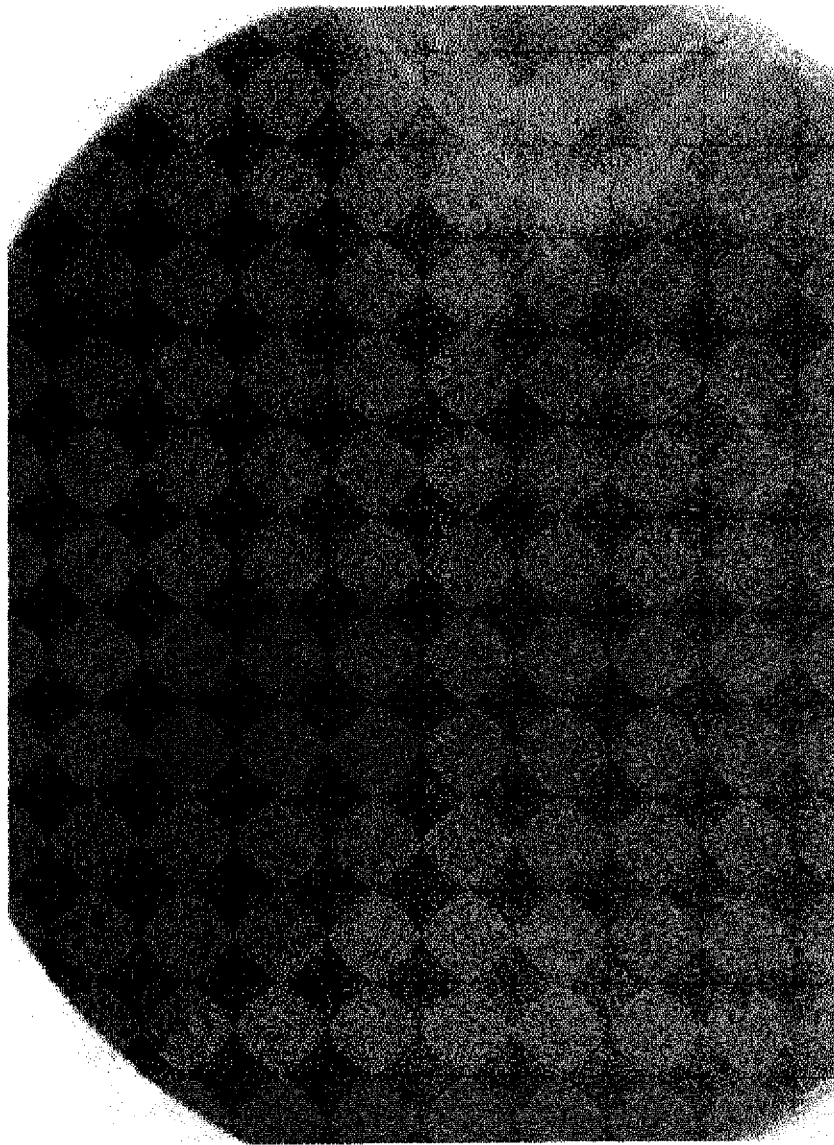
Figure 12:
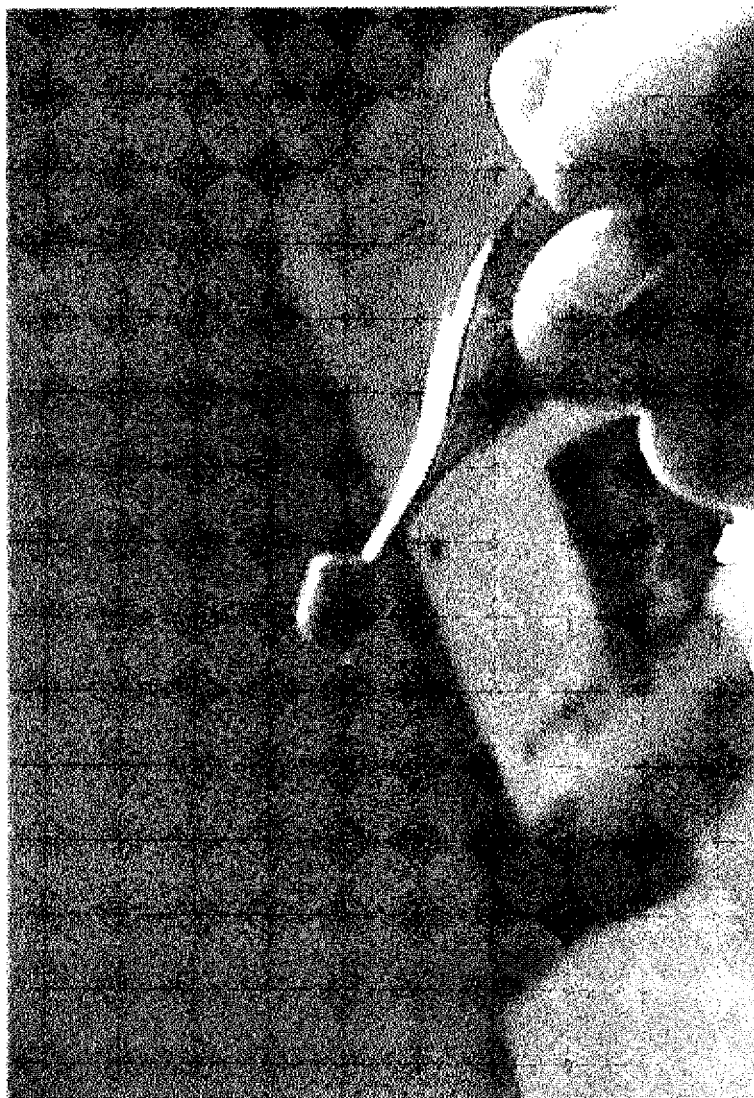
Figure 14:
Figure 15:
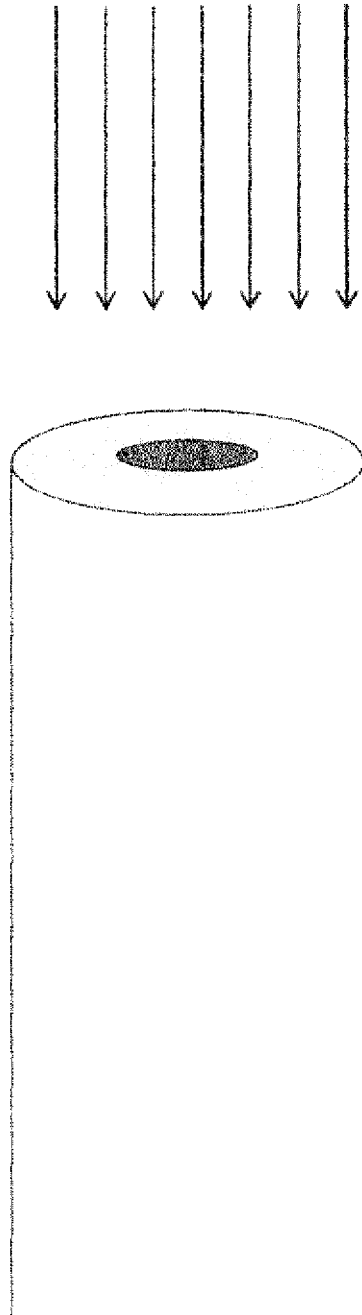
Figure 16:
Figure 17:
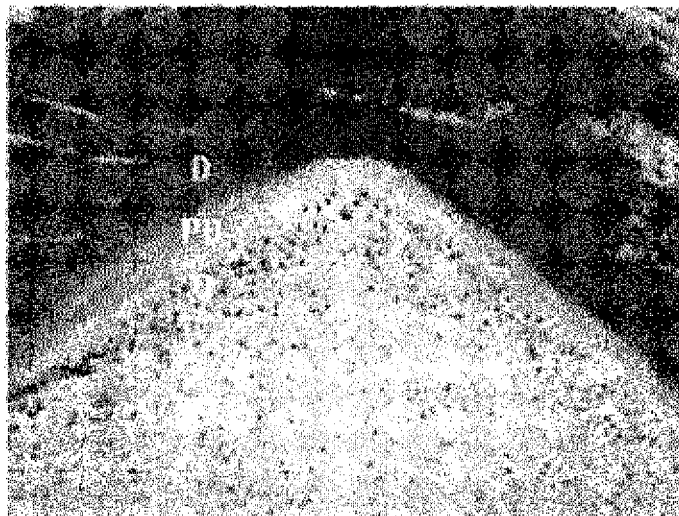
Figure 18:
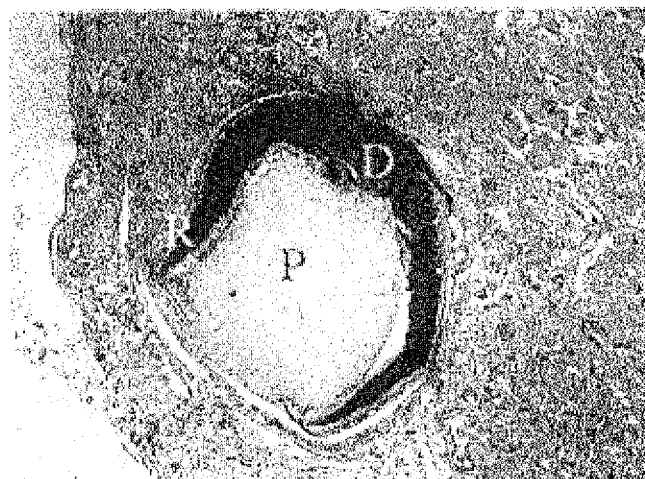
Figure 18:
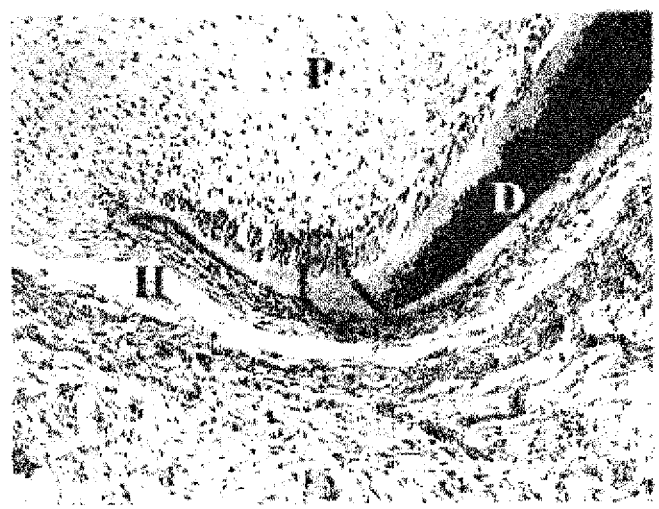
Figure 19:
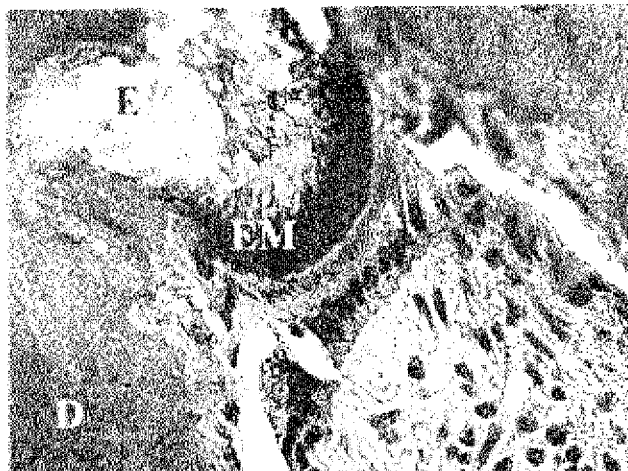
Figure 19:
Figure 20:
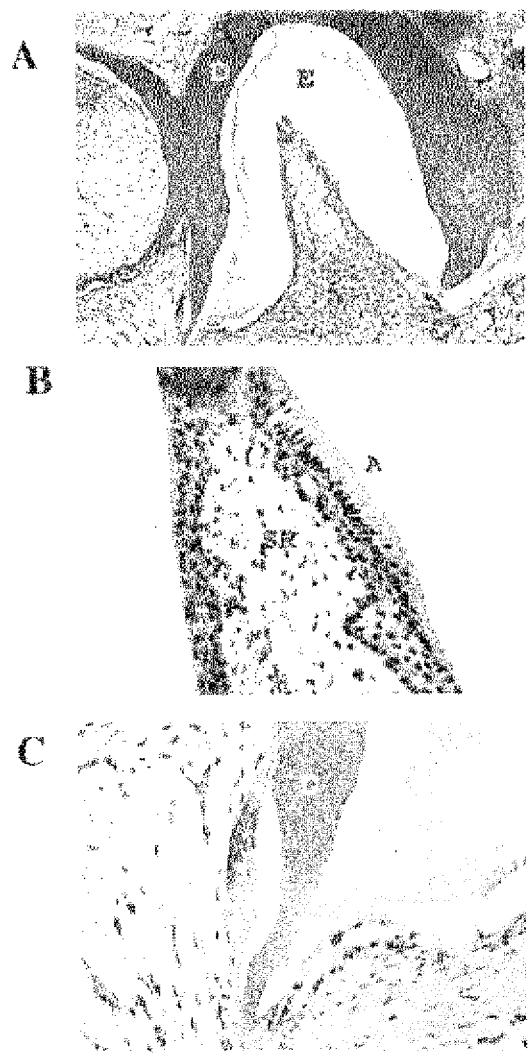

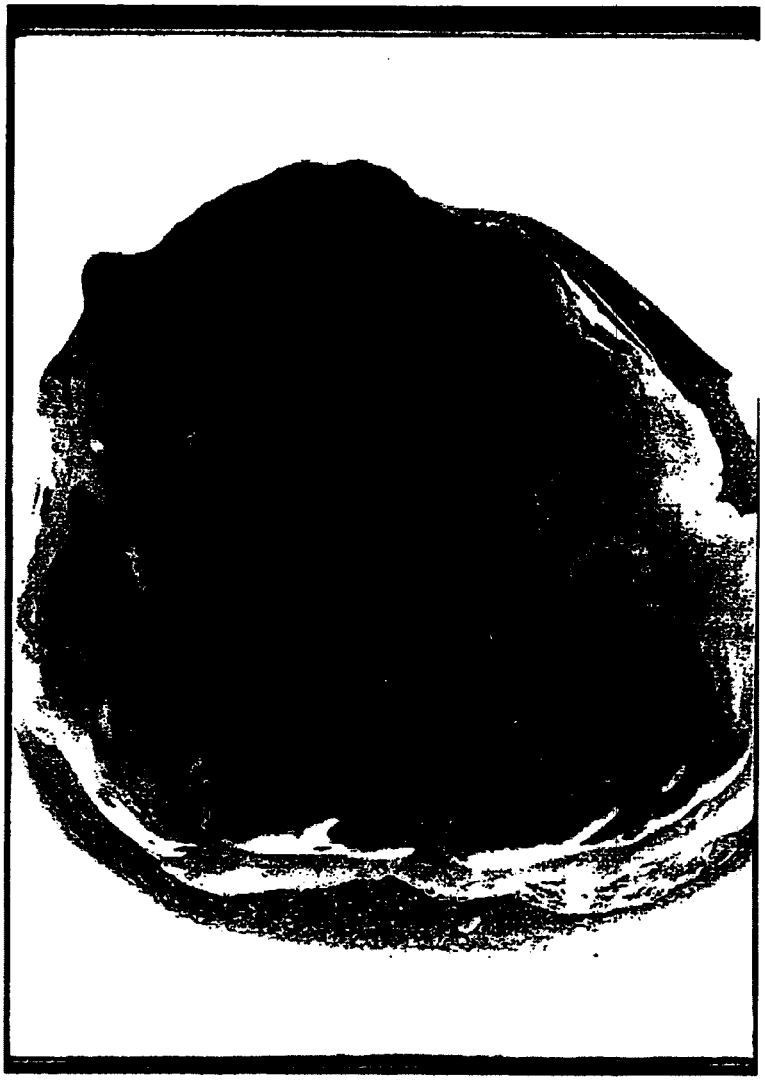
Fig. 14 Dissected Tooth Tissue Cysts - 7.5 Weeks

Goldner's Stain
Green = mineralized tissue

A

B

A

B

UNITED STATES PATENT AND TRADEMARK OFFICE
CERTIFICATE OF CORRECTION

| | | |
|---|---|---|
| PATENT NO. | : 6,899,915 B2 | |
| APPLICATION NO. | : 09/997734 | |
| DATED | : May 31, 2005 | |
| INVENTOR(S) | : Dunn | |

It is certified that error appears in the above-identified patent and that said Letters Patent is hereby corrected as shown below:

Delete Title page illustrating figure, and substitute new Title page illustrating figure attached.

Delete drawing sheets 1-20, and substitute drawing sheets 1-20, with the attached sheets.

Signed and Sealed this

Thirtieth Day of June, 2009

JOHN DOLL
*Acting Director of the United States Patent and Trademark Office*

(12) United States Patent
Yelick et al.

(10) Patent No.: US 6,899,915 B2
(45) Date of Patent: May 31, 2005

(54) METHODS AND COMPOSITIONS FOR CULTURING A BIOLOGICAL TOOTH

(75) Inventors: Pamela C. Yelick, Concord, MA (US); John D. Bartlett, Acton, MA (US); Joseph P. Vacanti, Winchester, MA (US); Bjorn R. Olsen, Milton, MA (US); Phillip Stashenko, Medfield, MA (US)

(73) Assignees: President and Fellows of Harvard College, Cambridge, MA (US); General Hospital Corporation, Boston, MA (US); Forsyth Dental Infirmary for Children, Inc., Boston, MA (US)

( * ) Notice: Subject to any disclaimer, the term of this patent is extended or adjusted under 35 U.S.C. 154(b) by 0 days.

(21) Appl. No.: 09/997,734

(22) Filed: Nov. 29, 2001

(65) Prior Publication Data
US 2002/0119180 A1 Aug. 29, 2002

Related U.S. Application Data
(60) Provisional application No. 60/253,891, filed on Nov. 29, 2000.

(51) Int. Cl.⁷ .................................................. A61C 13/08
(52) U.S. Cl. ................. 427/2.26; 433/202.1; 433/204; 264/19; 523/115
(58) Field of Search ................. 427/2.26, 2.27, 433/202.1, 204, 215, 223; 264/19; 523/115, 521/50, 51, 55; 514/21; 424/435; 623/23.58, 23.72, 23.75

(56) References Cited

U.S. PATENT DOCUMENTS

| | | | | |
|---|---|---|---|---|
| 5,098,891 A | * | 3/1992 | Hammarstrom et al. | 514/21 |
| 5,418,221 A | * | 5/1995 | Hammarstrom et al. | 514/21 |
| 5,863,297 A | * | 1/1999 | Walter et al. | 623/17.18 |
| 5,885,829 A | * | 3/1999 | Mooney et al. | 435/325 |
| 6,488,503 B1 | * | 12/2002 | Lichkus et al. | 433/202.1 |
| 2002/0022883 A1 | * | 2/2002 | Burg | 623/8 |
| 2002/0192198 A1 | * | 12/2002 | Elia | 424/93.21 |

OTHER PUBLICATIONS

"Annual Industry Report," *Implant Dentistry*, 9(3):192–194 (2000).
Baba et al., "Determination of enamel protein synthesized by recombined mouse molar tooth germs in organ culture," *Archives of Oral Biology* 41:215–219 (1996).
Backman et al., "Amelogenesis imperfecta: prevalence and incidence in a northern Swedish country," *Community Dent Oral Epidemiol*, 14(1):43–47 (1986).
Choi et al., "Studies of brush border enzymes, basement membrane components, and electrophysiology of tissue-engineered neointestine," *J. Pediatr. Surg.* 33:991–6; discussion 996–997 (1998).

(Continued)

*Primary Examiner*—James J. Seidleck
*Assistant Examiner*—Melanie Bissett
(74) *Attorney, Agent, or Firm*—Banner & Witcoff, Ltd.

(57) ABSTRACT

Tooth tissues include the pulp mesenchyme that forms the dentin and an epithelium that is responsible for enamel formation. Cells from these tissues were obtained from porcine third molars and were seeded onto a biodegradable scaffold composed of a polyglycolic acid—polylactic acid copolymer. Cell polymer constructs were then surgically implanted into the omentum of athymic nude rats so that the constructs would have a blood supply and these tissues were allowed to develop inside the rats. Infrequently, columnar epithelial cells were observed as a single layer on the outside of the dentin-like matrix similar to the actual arrangement of ameloblasts over dentin during early tooth development. Developing tooth tissues derived from such cell polymer constructs could eventually be surgically implanted into the gum of an edentulous recipient where the construct would receive a blood supply and develop to maturity, providing the recipient with a biological tooth replacement.

54 Claims, 20 Drawing Sheets

Tooth Scaffolds

PGA + PLLA

SEM-PLGA Scaffold + Salt

Figure 5:
FIGS. 5 and 6 show removal of a porcine third molar.
Figure 5:
Figure 6:
Figure 6:
Figure 8:
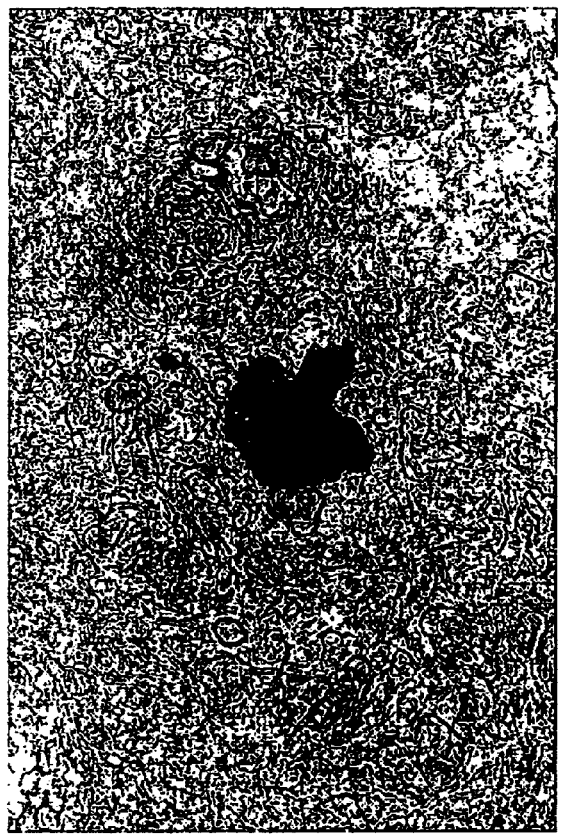
FIG. 8 shows tissue culture with a Von Kossa stain.
Figure 8:
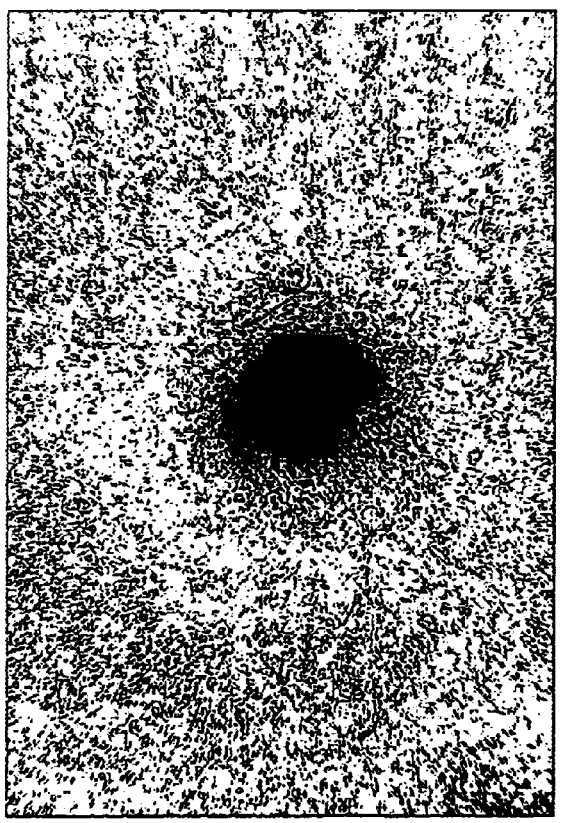

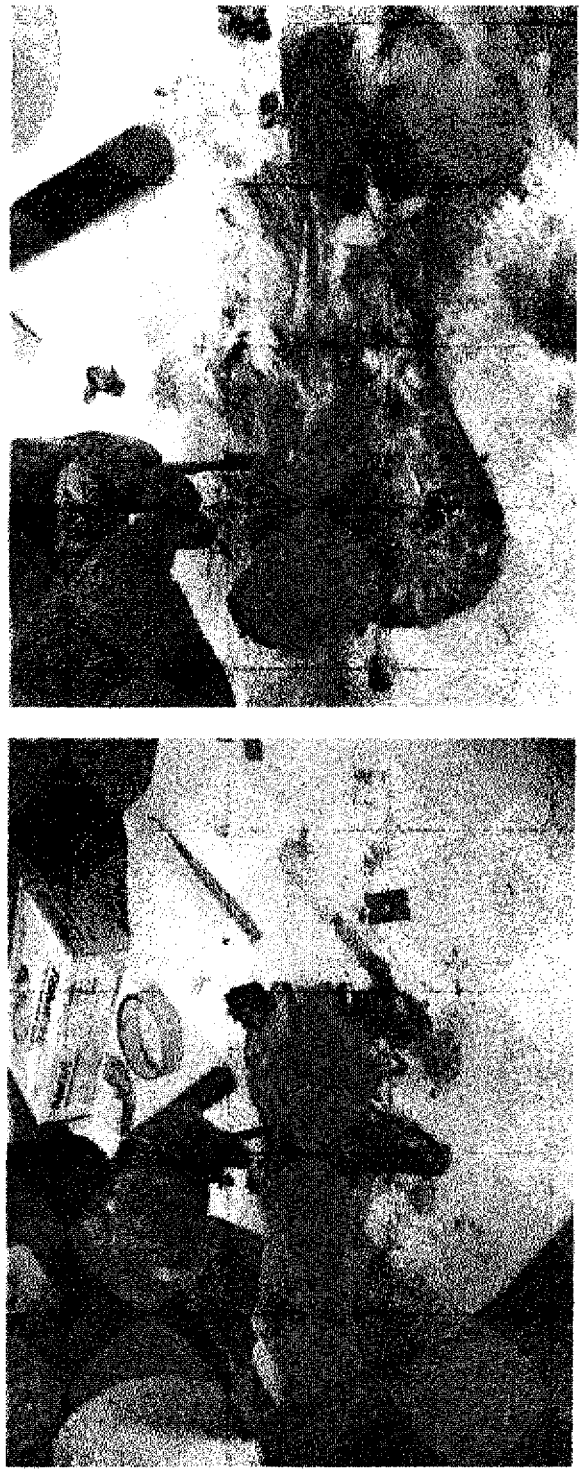
Fig. 5 — Removal of Porcine Third Molar

Rat Radiographs - Human Tooth

Rat Radiographs - Implant, 7.5 weeks

Fig. 11 — Dissection of Tissue

Figure 12:
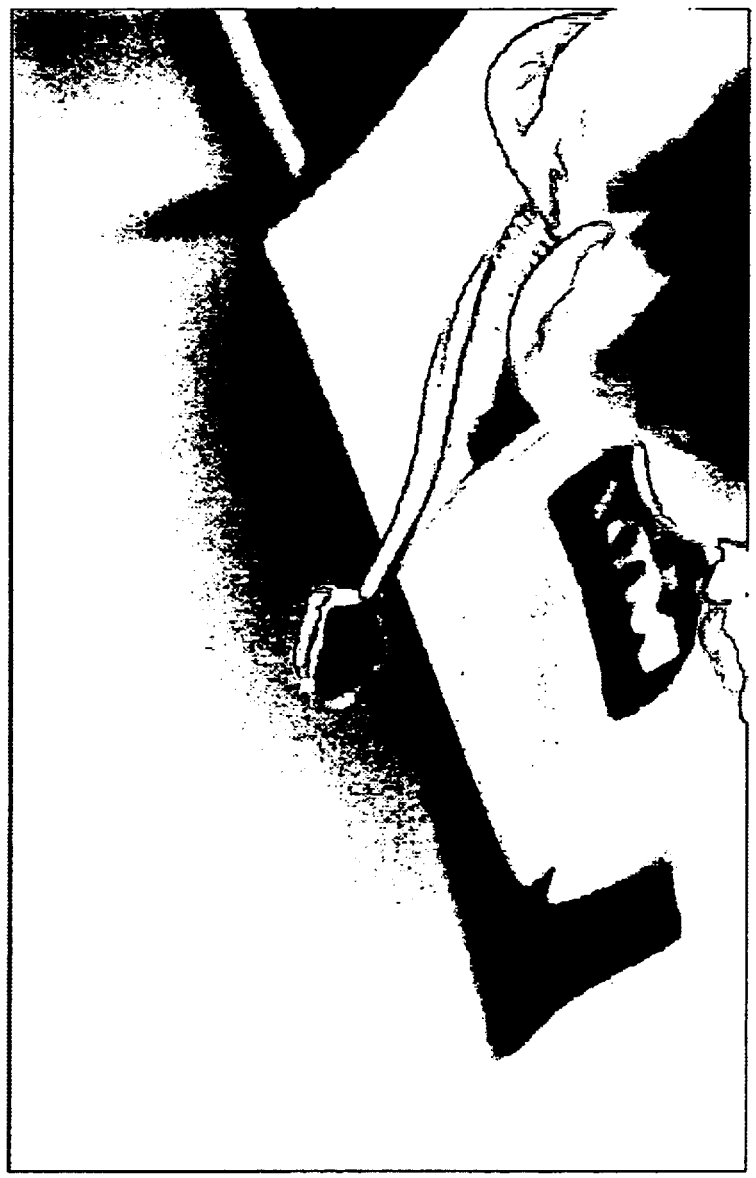

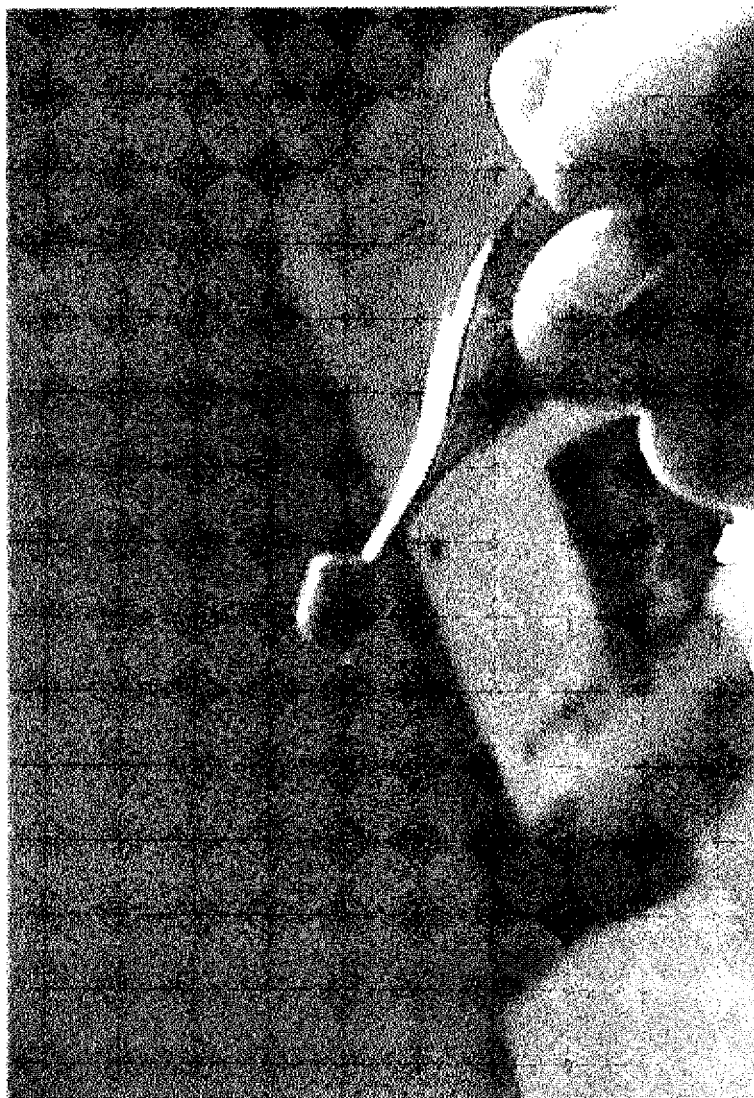
Fig. 12 Dissection of Tooth Tissue 7.5 weeks

Dissected Tooth Tissue - 7.5 Weeks

Dissected Tooth Tissue Cysts - 7.5 Weeks

Goldner's Stain
Green = mineralized tissue

A

B

A

B

UNITED STATES PATENT AND TRADEMARK OFFICE
CERTIFICATE OF CORRECTION

| | | |
|---|---|---|
| PATENT NO. | : 6,899,915 B2 | Page 1 of 22 |
| APPLICATION NO. | : 09/997734 | |
| DATED | : May 31, 2005 | |
| INVENTOR(S) | : Dunn | |

It is certified that error appears in the above-identified patent and that said Letters Patent is hereby corrected as shown below:

Delete Title page illustrating figure, and substitute new Title page illustrating figure attached.

Delete drawing sheets 1-20, and substitute drawing sheets 1-20, with the attached sheets.

This certificate supersedes the Certificates of Correction issued August 8, 2006 and June 30, 2009.

Signed and Sealed this

Fourth Day of August, 2009

JOHN DOLL
*Acting Director of the United States Patent and Trademark Office*

(12) United States Patent
Yelick et al.

(10) Patent No.: US 6,899,915 B2
(45) Date of Patent: May 31, 2005

(54) METHODS AND COMPOSITIONS FOR CULTURING A BIOLOGICAL TOOTH

(75) Inventors: Pamela C. Yelick, Concord, MA (US); John D. Bartlett, Acton, MA (US); Joseph P. Vacanti, Winchester, MA (US); Bjorn R. Olsen, Milton, MA (US); Phillip Stashenko, Medfield, MA (US)

(73) Assignees: President and Fellows of Harvard College, Cambridge, MA (US); General Hospital Corporation, Boston, MA (US); Forsyth Dental Infirmary for Children, Inc., Boston, MA (US)

(*) Notice: Subject to any disclaimer, the term of this patent is extended or adjusted under 35 U.S.C. 154(b) by 0 days.

(21) Appl. No.: 09/997,734

(22) Filed: Nov. 29, 2001

(65) Prior Publication Data

US 2002/0119180 A1 Aug. 29, 2002

Related U.S. Application Data

(60) Provisional application No. 60/253,891, filed on Nov. 29, 2000.

(51) Int. Cl.⁷ .................................................. A61C 13/08
(52) U.S. Cl. ............ 427/2.26; 433/202.1; 433/204; 264/19; 523/115
(58) Field of Search ................... 427/2.26, 2.27, 433/202.1, 204, 215, 223; 264/19; 523/115, 521/50, 51, 55; 514/21; 424/435; 623/23.58, 23.72, 23.75

(56) References Cited

U.S. PATENT DOCUMENTS

| 5,098,891 A | * | 3/1992 | Hammarstrom et al. ...... 514/21 |
| 5,418,221 A | * | 5/1995 | Hammarstrom et al. ...... 514/21 |
| 5,863,297 A | * | 1/1999 | Walter et al. ............ 623/17.18 |
| 5,885,829 A | * | 3/1999 | Mooney et al. ............. 435/325 |
| 6,488,503 B1 | * | 12/2002 | Lichkus et al. ............ 433/202.1 |
| 2002/0022883 A1 | * | 2/2002 | Burg ........................... 623/8 |
| 2002/0192198 A1 | * | 12/2002 | Elia ......................... 424/93.21 |

OTHER PUBLICATIONS

"Annual Industry Report," *Implant Dentistry*, 9(3):192-194 (2000).
Baba et al., "Determination of enamel protein synthesized by recombined mouse molar tooth germs in organ culture," *Archives of Oral Biology* 41:215-219 (1996).
Backman et al., "Amelogenesis imperfecta: prevalence and incidence in a northern Swedish country," *Community Dent Oral Epidemiol*, 14(1):43-47 (1986).
Choi et al., "Studies of brush border enzymes, basement membrane components, and electrophysiology of tissue-engineered neointestine," *J. Pediatr. Surg.* 33:991-6; discussion 996-997 (1998).

(Continued)

*Primary Examiner*—James J. Seidleck
*Assistant Examiner*—Melanie Bissett
(74) *Attorney, Agent, or Firm*—Banner & Witcoff, Ltd.

(57) ABSTRACT

Tooth tissues include the pulp mesenchyme that forms the dentin and an epithelium that is responsible for enamel formation. Cells from these tissues were obtained from porcine third molars and were seeded onto a biodegradable scaffold composed of a polyglycolic acid—polylactic acid copolymer. Cell polymer constructs were then surgically implanted into the omentum of athymic nude rats so that the constructs would have a blood supply and these tissues were allowed to develop inside the rats. Infrequently, columnar epithelial cells were observed as a single layer on the outside of the dentin-like matrix similar to the actual arrangement of ameloblasts over dentin during early tooth development. Developing tooth tissues derived from such cell polymer constructs could eventually be surgically implanted into the gum of an edentulous recipient where the construct would receive a blood supply and develop to maturity, providing the recipient with a biological tooth replacement.

54 Claims, 20 Drawing Sheets

Tooth Scaffolds

PGA + PLLA

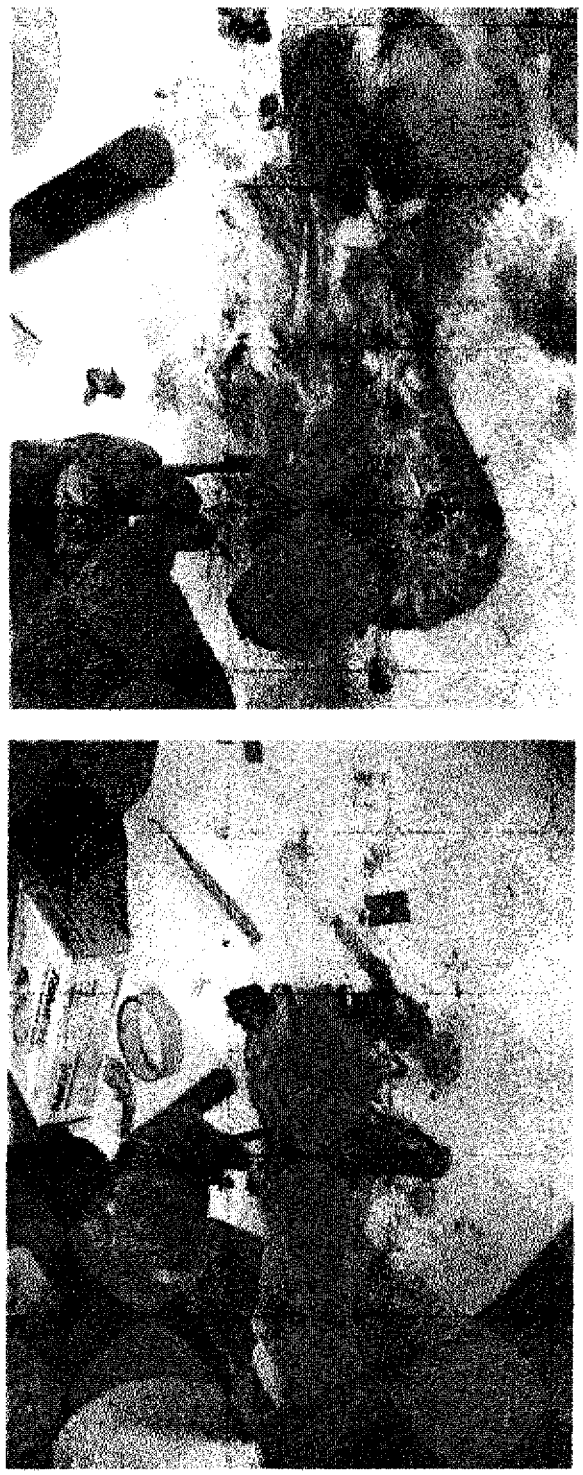
Fig. 5 — Removal of Porcine Third Molar

Removal of Porcine Third Molar

Figure 9:
FIG. 9 shows rat radiographs of a human tooth.
Figure 10:
FIG. 10 shows rat radiographs of an implant, 7½ weeks.

Fig. 9 — Rat Radiographs - Human Tooth

Rat Radiographs - Implant, 7.5 weeks

Fig. 11 — Dissection of Tissue

Dissection of Tooth Tissue
7.5 weeks

Figure 13:
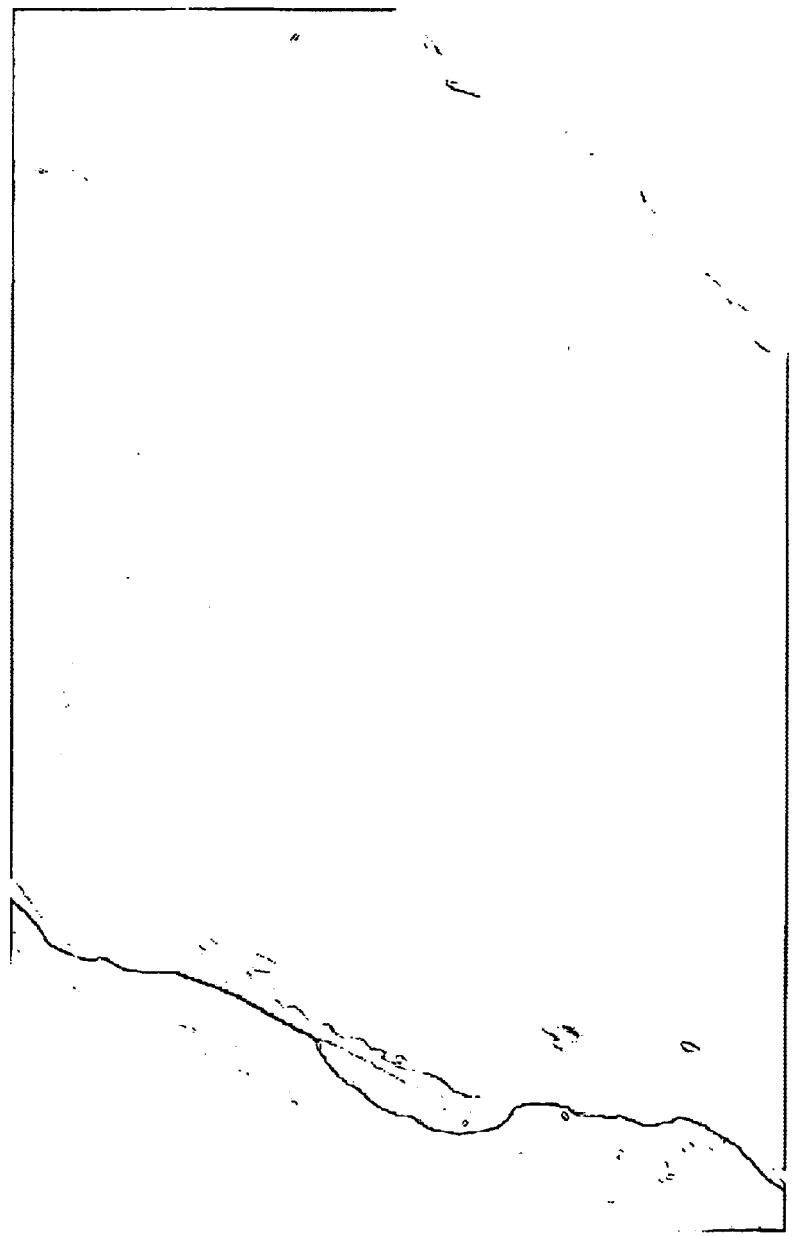
FIGS. 13 and 14 show dissected tooth tissue cysts, 7½ weeks.
Figure 15:
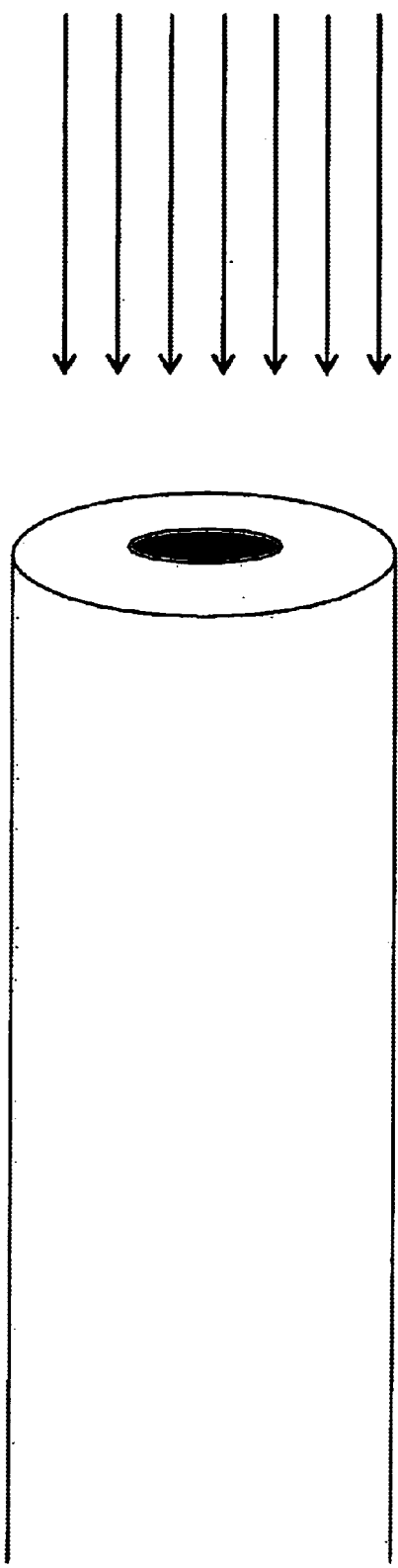
FIG. 15 is a schematic drawing of tissue sectioning.
Figure 16:
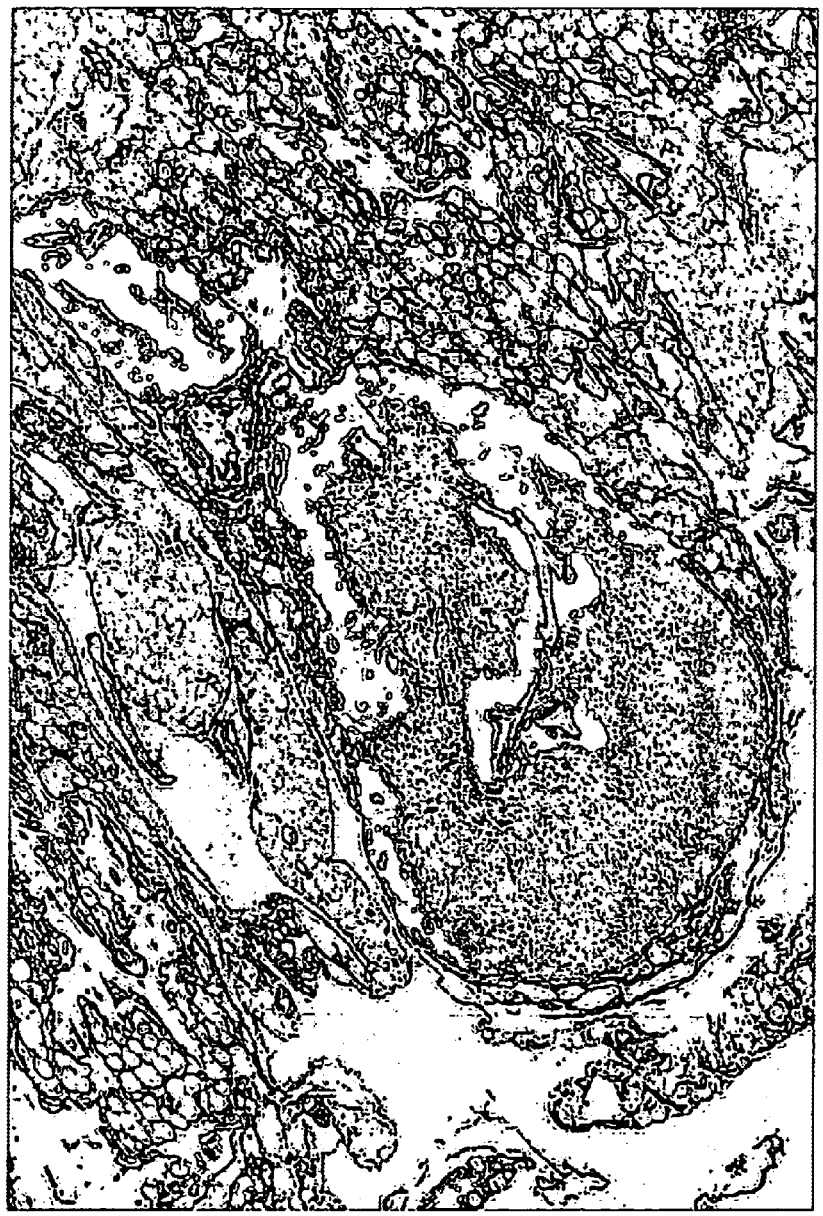
FIG. 16 shows sectioned tissue with Goldner's stain.

Fig. 13  Dissected Tooth Tissue - 7.5 Weeks

Dissected Tooth Tissue Cysts - 7.5 Weeks

Goldner's Stain
Green = mineralized tissue

A

B

A

B